US006403647B1

(12) United States Patent
Perrine

(10) Patent No.: US 6,403,647 B1
(45) Date of Patent: Jun. 11, 2002

(54) PULSED ADMINISTRATION OF COMPOSITIONS FOR THE TREATMENT OF BLOOD DISORDERS

(75) Inventor: Susan P. Perrine, 45 Beaver Rd., Weston, MA (US) 02493

(73) Assignee: Susan P. Perrine, Weston, MA (US)

( * ) Notice: Subject to any disclaimer, the term of this patent is extended or adjusted under 35 U.S.C. 154(b) by 0 days.

(21) Appl. No.: 09/557,384

(22) Filed: Apr. 25, 2000

Related U.S. Application Data

(60) Continuation-in-part of application No. 09/344,870, filed on Jun. 28, 1999, now abandoned, which is a division of application No. 08/687,670, filed on Jul. 26, 1996, now Pat. No. 5,939,456.

(51) Int. Cl.$^7$ ..................... A61K 31/185; A61K 31/19; A61K 31/215; A61P 7/06
(52) U.S. Cl. ..................... 514/575; 514/576; 514/578; 514/563; 514/568; 514/538; 514/629; 514/546; 514/554; 514/507
(58) Field of Search ................. 514/576, 578, 514/563, 568, 538, 629, 546, 554, 507, 575

(56) References Cited

U.S. PATENT DOCUMENTS

| | | | |
|---|---|---|---|
| 4,613,616 A | * | 9/1986 | Winston ..................... 514/507 |
| 4,723,958 A | | 2/1988 | Pope et al. |
| 4,747,825 A | | 5/1988 | Linkie et al. |
| 4,820,711 A | | 4/1989 | Pearlman |
| 4,849,426 A | | 7/1989 | Pearlman |
| 4,851,229 A | | 7/1989 | Magruder et al. |
| 4,853,388 A | | 8/1989 | Pearlman |
| 4,948,592 A | | 8/1990 | Ayer et al. |
| 4,965,251 A | | 10/1990 | Stamatoyannopoulos |
| 5,403,590 A | | 4/1995 | Forse |
| 5,912,269 A | * | 6/1999 | Tung ..................... 514/547 |

FOREIGN PATENT DOCUMENTS

WO   WO 95/11699   5/1995

OTHER PUBLICATIONS

Abstract of ASH Annual Meeting, Seattle, Washington, Dec. 1–5, 1995; Liakopoulou et al., "Structural Features of Short Chain Fatty Acid–Derived Inducers of Fetal Hemoglobin".
Abstract of ASH Annual Meeting Seattle, Washington, Dec. 1–5, 1995; Grossi et al., "Effects of Monosaccharide Esters of Butyric Acid on the Synthesis of Hemoglobin T Chain an Erythroleukemia Cell Line".
Abstract of ASH Annual Meeting, Seattle, Washington, Dec. 1–5, 1995; Zituik et al., "The Silencing of γ–Globin Gene Exin a β–Globin Locus Yac can be Arrested by a α–Aminobutyric Acid".

* cited by examiner

Primary Examiner—Evelyn Mei Huang
(74) Attorney, Agent, or Firm—Nixon Peabody LLP

(57) ABSTRACT

The invention relates to novel compositions and to methods for the pulsed administration of compositions to a patient or to cells in vitro for the treatment of human blood disorders. Compositions contain chemical compounds that stimulate the expression of fetal hemoglobin and/or stimulate the proliferation of red blood cells, white blood cells and platelets in patients and ex vivo for reconstitution of hematopoiesis in vivo. These methods are useful to treat or prevent the symptoms associated with anemia, sickle cell disease, thalassemia and other blood disorders. The, invention also relates to methods for the pulsed administration of compositions to patients for the treatment and prevention of cell proliferative disorders including deficiencies such as cytopenia and malignancies such as viral-induced tumors, other forms of neoplasia and for expansion of cells for hematopoietic transplantation. Pulsed administration has been shown to be more effective than continuous therapy in patients tested.

5 Claims, 10 Drawing Sheets

PULSED ADMINISTRATION OF COMPOSITIONS FOR THE TREATMENT OF BLOOD DISORDERS

This application is a continuation-in-part of co-pending application Ser. No. 09/344,870, filed Jun. 28, 1999 abandoned, which is hereby incorporated herein by reference, which is a divisional application of application Ser. No. 08/687,670, filed Jul. 26, 1996 U.S. Pat. No. 5,939,456.

RIGHTS IN THE INVENTION

This invention was made with support from the United States government under grant numbers HL-37118 and HL-15157, awarded by the National Heart, Lung and Blood Institute of the National Institutes of Health, and grant number 000831, awarded by the United States Food and Drug Administration, and the United States government has certain rights in the invention.

BACKGROUND OF THE INVENTION

1. Field of the Invention

The invention relates to methods for the treatment and prevention of blood disorders such as anemia, neutropenia, thrombocytopenia, thalassemia and sickle cell disease. These methods comprise the administration of compositions that stimulate the expression of a globin protein and, in particular, fetal hemoglobin, or the proliferation or development of hemoglobin expressing, myeloid cells or megakaryocytic cells.

2. Description of the Background

The major function of red blood cells is to transport oxygen to tissues of the body. Minor functions include the transportation of nutrients, intercellular messages and cytokines, and the absorption of cellular metabolites. Anemia, or a loss of red blood cells or red blood cell capacity, can be grossly defined as a reduction in the ability of blood to transport oxygen. Anemia can be measured by determining a patient's red blood cell mass or hematocrit. Hematocrit values are indirect, but fairly accurate measures of the total hemoglobin concentration of a blood sample. Anemia, as measured by a reduced hematocrit, may be chronic or acute. Chronic anemia may be caused by extrinsic red blood cell abnormalities, intrinsic abnormalities or impaired production of red blood cells. Extrinsic or extracorpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. In addition, infections by parasites such as Plasmodium, chemical injuries from, for example, lead poisoning, and sequestration in the mononuclear system such as by hyperspienism can result in red blood cell disorders and deficiencies.

Impaired red blood cell production can occur by disturbing the proliferation and differentiation of the stem cells or committed cells. Some of the more common diseases of red cell production include aplastic anemia, hypoplastic anemia, pure red cell aplasia and anemia associated with renal failure or endocrine disorders. Disturbances of the proliferation and differentiation of erythroblasts include defects in DNA synthesis such as impaired utilization of vitamin $B_{12}$ or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Intrinsic abnormalities include both hereditary and acquired disorders. Acquired disorders are those which have been induced through, for example, a membrane defect such as paroxysmal nocturnal hemoglobinuria. Hereditary disorders include disorders of membrane cytoskeleton such as spherocytosis and elliptocytosis disorders of lipid synthesis such as an abnormally increased lecithin content of the cellular membrane, red cell enzyme deficiencies such as deficiencies of pyruvate kinase, hexokinase, glutathione synthetase and glucose-6-phosphate dehydrogenase. Although red blood cell disorders may be caused by certain drugs and immune system disorders, the majority are caused by genetic defects in the expression of hemoglobin. Disorders of hemoglobin synthesis include deficiencies of globin synthesis such as thalassemia syndromes and structural abnormalities of globin such as sickle cell syndromes and syndromes associated with unstable hemoglobins.

Mammalian globin gene expression is highly regulated during development. The basic structure of the $\alpha$ and $\beta$ globin genes are similar as are the basic steps in synthesis of $\alpha$ and $\beta$ globin. There are at least five human $\alpha$ globin genes located on chromosome 16 including two adult $\alpha$ globin genes of 141 amino acids that encode identical polypeptides which differ only in their 3'-untranslated regions, one embryonic $\alpha$ gene, zeta ($\zeta$), and at least two pseudo-alpha genes, psi zeta (P$\beta$) and omega alpha ($\omega\alpha$). The human $\beta$ globin gene cluster includes one embryonic gene, epsilon ($\epsilon$), two adult beta globin genes, beta ($\beta$) and delta ($\delta$), two fetal beta globin genes G-gamma (G-$\gamma$) and A-gamma (A-$\gamma$), which differ by only one amino acid, and at least one pseudo-beta gene, psi beta (P$\beta$). All are expressed from a single 43 kilobase segment of human chromosome 11 (E. F. Fritsch et al., Nature 279:598–603, 1979).

Hemoglobin A comprises four protein chains, two alpha chains and two beta chains ($\alpha_2\beta_2$), interwoven together, each with its own molecule of iron and with a combined molecular weight of about 68 kD. The hemoglobin macromolecule is normally glycosylated and upon absorbing oxygen from the lungs transforms into oxyhemoglobin (HbO$_2$). There are at least six distinct forms of hemoglobin, each expressed at various times during development. Hemoglobin in the embryo is found in at least three forms, Hb-Gower 1 ($\zeta_2$), Hb-Gower 2 ($\alpha_2\gamma_2$), and Hb-Portand ($\zeta_2\gamma_2$). Hemoglobin in the fetus comprises nearly totally HbF ($\alpha_2\gamma_2$), whereas hemoglobin in the adult contains about 96% HbA ($\alpha_2\beta_2$), about 3% HbA$_2$ ($\alpha_2\zeta_2$) and about 1% fetal HbF ($\alpha_2\gamma_2$). The embryonic switch of globin expression from $\zeta$ to $\alpha$ and from $\epsilon$ to $\gamma$ begins in the yolk sac. However, chains of embryonic $\zeta$ and $\epsilon$ have been found in the fetal liver and complete transition to the fetal form does not occur until late in fetal development. The fetal switch from $\gamma$ to $\beta$ begins later in erythropoiesis with the amount of $\gamma$ globin produced increasing throughout gestation. At birth, $\beta$ globin accounts for about 40% of non-$\alpha$ globin chain synthesis and thereafter continues to rapidly increase. Neither the switch from embryonic to fetal or fetal to adult appears to be controlled through cell surface or known cytokine interactions. Control seems to reside in a developmental clock with the switch occurring at times determined only by the stage of fetal development.

Defects or mutations in globin chain expression are common. Some of these genetic mutations pose no adverse or only minor consequences to the person, however, most mutations prevent the formation of an intact or normal hemoglobin molecule through a functional or structural inability to effectively bind iron, an inability of the chains or chain pairs to effectively or properly interact, an inability of the molecule to absorb or release oxygen, a failure to express sufficient quantities of one or more globin chains or a combination of these malfunctions. For example, substitutions of valine for glutamic acid at the sixth position of the β chain produces HbS and was found to occur in about 30% of black Americans. In the HbS heterozygote, only about 40% of total hemoglobin is HbS with the remainder being the more normal HbA.

Upon deoxygenation, HbS molecules undergo aggregation and polymerization ultimately leading to a morphological distortion of the red cells which acquire a sickle or holly-leaf shape. Sickling has two major consequences, a chronic hemolytic anemia and an occlusion of small blood vessels that results in ischemic damage to tissues. Further, when exposed to low oxygen tensions, polymerization converts HbS hemoglobin from a free-flowing liquid to a viscous gel. Consequently, the degree of pathology associated with sickle cell anemia can be correlated with the relative amount of HbS in the patient's system.

Individuals with severe sickle cell anemia develop no symptoms until about five to six months after birth. In these infants it was determined that fetal hemoglobin did not interact with HbS and, as long as sufficient quantities were present, could modulate the effects of HbS disease. This modulating effect of β globin is also observed with other β globin disorders, such as HbC and HbD, and other mutations of the β chain. HbS polymerization is also significantly affected by the hemoglobin concentration of the cell. The higher the HbS concentration, the greater the chances for contact between two or more HbS molecules. Dehydration increases hemoglobin concentration and greatly facilitates sickling.

To some extent, sickling is a reversible phenomenon. With increased oxygen tensions, sickled cells depolymerize. This process of polymerization-depolymerization is very damaging to red cell membranes and eventually leads to irreversibly sickled cells (ISC) which retain their abnormal shape even when fully oxygenated. The average ISC survives for about 20 days in the body, as compared to the normal 120 day life span. Individuals with HbS syndromes have frequent infections, chronic hemolysis with a striking reticulocytosis and hyperbilirubinemia. The course of the disease is typically punctuated with a variety of painful crises called vaso-occlusive crises. These crises represent episodes of hypoxic injury and infarction in the organs, abdomen, chest, extremities or joints. Leg ulcers are an additional manifestation of the vaso-occlusive tendency of this disease. Central nervous system involvement is common producing seizures and even strokes. Aplastic crises, also common, represent a temporary cessation of bone marrow activity and may be triggered by infections, folic acid deficiency or both. Crises are episodic and reversible, but may be fatal. Damage from crisis episodes tends to be cumulative and even in those individuals with milder forms of sickle cell disorders, life-spans can be greatly reduced. Absent alternative intervention, patients typically die before the age of 30.

The thalassemia syndromes are a heterogenous group of disorders all characterized by a lack of or a decreased synthesis of the globin chains of HbA. Deficiencies of β-globin expression are referred to as β-thalassemias and deficiencies of α-globin, α-thalassemias. The hemolytic consequences of deficient globin chain synthesis result from decreased synthesis of one chain and also an excess of the complementary chain. Free chains tend to aggregate into insoluble inclusions within erythrocytes causing premature destruction of maturing erythrocytes and their precursors, ineffective erythropoiesis, and the hemolysis of mature red blood cells. The underlying defects of hemoglobin synthesis have been elucidated over the years and largely reside in the nucleic acid sequences which express or control the expression of α or β globin protein.

Surprisingly, α-thalassemias tend to be less severe than β thalassemias. Homozygous pairs of β chains are believed to be more soluble than those derived from unpaired α chains. Consequently, the effects associated with free or improperly paired globin chains, which correlate with at least half of the clinical pathology associated with thalassemia, are minimized.

Hemoglobin H disease, a more severe form of α thalassemia, is a deletion of three of the four α globin genes. It is rarely found in those of African origin, but mostly in Asians. With only a single α gene, α chain expression is markedly depressed and there is an excess of β chains forming tetramers called HbH hemoglobin. HbH is unable to withstand oxidative stress and precipitates with vessels or is removed by the spleen. The most severe form of α thalassemia is hydrops fetalis and results from a deletion of all α globin genes. In the fetus, tetramers of γ globin develop (Hb Barts) that have an extremely high oxygen affinity and are unable to release oxygen to the tissues. Severe tissue anoxia results and leads to intrauterine fetal death.

Fetal β-type globin, or γ globin, is expressed in the earliest stages of mammalian development and persists until about 32 to 34 weeks of gestation. At this stage, the adult forms of β globin begin to be expressed and substitute for the fetal proteins. Studies correlating clinical hematological results with the locations of various mutations that correspond to switching indicate that a region located upstream of the 5'-end of the δ-gene may be involved in the cis suppression of γ-gene expression in adults (E. F. Fritsch et al., Nature 279:598–603, 1979). The reason for this switch from fetal to adult protein is unknown and does not appear to provide any significant benefit to the adult.

Each β globin gene comprises three exons which encode about 146 amino acids, two introns and a 5'-untranslated region containing the promoter sequences. Biosynthesis of β globin begins with transcription of the entire gene followed with RNA processing of the message, removal of the introns by splicing, poly A addition, capping and post-transcriptional modifications. The mature mRNA molecule is exported from the nucleus and translated into β globin. Defects in each of these functions have been found associated with specific thalassemias. Identified mutations include single-nucleotide deletions, insertions and substitutions, frame shift mutations, deletions of entire segments of coding or controlling regions, improper termination signals, aberrant splicing signals, and multiple mutations. β°-thalassemias are characterized by a complete absence of any β globin chains. β⁺-thalassemias are characterized by a detectable presence of a reduced amount of β chains.

There are three principal categories of β-thalassemia, thalassemia major, thalassemia intermedia and thalassemia minor. Patients with thalassemia minor may be totally asymptomatic and are genotypically β⁺/β or β°/β. Although red cell abnormalities can be detected, symptoms are mild. Thalassemia intermedia patients are most often genotypically β⁺/β⁺ or β°/β and present severe symptoms which can be alleviated with infrequent blood transfusions. In contrast, thalassemia major patients are genotypically β°/β°, β°/β⁺ or β⁺/β⁺, and require regular and frequent transfusions. Children suffer from severe growth retardation and die at an early age from the profound effects of anemia. Those that survive longer suffer from morphological changes. The face becomes distorted due to expansion of marrow within the bones of the skull, hepatosplenomegaly ensues, there is a delayed development of the endocrine organs including the sexual organs, and a progressive iron overload with secondary hemochromatosis.

There are two direct consequences of β-thalassemia. First, there is an inadequate formation of HbA and, therefore, an impaired ability to transport oxygen. There are also multiple effects attributable to an imbalance between α and β chain synthesis. Surprisingly, the pathological consequences of globin chain imbalance appears to be the more severe. Free α chains form unstable aggregates that precipitate within red cell precursors in the form of insoluble inclusions. These inclusions damage cellular membranes resulting in a loss of potassium. The cumulative effect of these inclusions on the red blood cells is an ineffective erythropoiesis. An estimated 70% to 85% of normoblasts in the marrow are eventually destroyed. Those that do escape immediate destruction are at increased risk of elimination by the spleen where macrophages remove abnormal cells. Further, hemolysis triggers an increased expression of erythropoietin which expands populations of erythroid precursors within bone marrow and leads to skeletal abnormalities. Another severe complication of β thalassemia is that patients tend to have an increased ability to absorb dietary iron. As most treatments for thalassemia involve multiple transfusions of red blood cells, patients often have a severe state of iron overload damaging all of the organs and particularly the liver. To reduce the amount of iron in their systems, iron chelators are typically administered. Although helpful, patients succumb at an average of between about 17 to 35 years of age to the cumulative effects of the disease and iron overload.

Genotypic variation in healthy individuals have been identified wherein adult β globin is not formed, but severe complications are avoided. These patients constituitively express fetal or γ globin protein in amounts sufficient to substitute for the missing β globin protein. This hereditary persistence of fetal hemoglobin (HPFH) may involve one or both of the fetal β-globin genes, A-γ and G-γ. Apparently, consistent production of either y-globin protein accomplishes the necessary functions, at least in the short term, of the abnormal or missing β-globin protein (R. Bernards et al., Nuc. Acids Res. 8:1521–34, 1980).

A variety of small molecules have been shown to effect hemoglobin or fetal globin expression. Early experiments demonstrated that acetate ($CH_3COOH$), propionate ($CH_3CH_2COOH$), butyrate ($CH_3CH_2CH_2COOH$) and isobutyrate ($CH_3CH(CH_3)COOH$) all induced hemoglobin synthesis in cultured Friend leukemia cells (E. Takahashi et al., Gann 66:577–80, 1977). Additional studies showed that polar compounds, such as acid amides, and fatty acids could stimulate the expression of both fetal and adult globin genes in murine erythroleukemia cells (U. Nudel et al., Proc. Natl. Acad. Sci. USA 74:1100–4, 1977). Hydroxyurea ($H_2NCONHOH$), another relatively small molecule, was found to stimulate globin expression (N. L. Letvin et al., N. Engl. J. Med. 310:869–73, 1984). Stimulation, however, did not appear to be very specific to fetal globin (S. Charache et al., Blood 69:109–16, 1987). Hydroxyurea is also a well-known carcinogen making its widespread and long term use as a pharmaceutical impractical.

Expression from the γ-globin genes has been successfully manipulated in vivo and in vitro using agents such as cytosine arabinoside (AraC), a cytotoxic agent that induces fetal reticulocyte production (P. Constantoulakis et al., Blood 74:1963–71, 1989), and 5-azacytidine (AZA), a well-known DNA methylase inhibitor (T. J. Ley et al., N. Engl. J. Med. 307:1469–75, 1982). Continuous intravenous administration of AZA produced a five- to seven-fold increase in γ globin mRNA of bone marrow cells (T. J. Ley et al., Blood 62:370–380, 1983). Additional studies have shown that there are significant alterations in the population of stem cells in the bone marrow after AZA treatment (A. T. Torrealba-De Ron et al., Blood 63:201–10, 1984). These experiments indicate that AZA's effects may be more attributable to reprogramming and recruitment of erythroid progenitor cells than to any direct effects on specific gene expression. Many of these agents including AZA, AraC and hydroxyurea are myelotoxic, carcinogenic or teratogenic making long-term use impractical.

One of the major breakthroughs in the treatment of hemoglobinopathies was made when it was discovered that butyric acid (butanoic acid; $CH_3CH_2CH_2COOH$) accurately and specifically stimulated transcription of the human fetal (γ) globin gene (G. A. Partington et al., EMBO J. 3:2787–92, 1984). These findings were quickly confirmed in vivo wherein it was shown that pharmacological doses of butyric acid greatly increased expression of fetal globin in adult chickens rendered anemic by injections with phenylhydrazine (G. D. Ginder et al., Proc. Natl. Acad. Sci. USA 81:3954–58, 1984). Selective transcriptional activation was again thought to be due to hypo-methylation of the embryonic gene (L. J. Burns et al., Blood 72:1536–42, 1988). Others speculated that histone acetylation, a known effect of butyric acid, may be at least partly responsible for increased fetal gene expression (L. J. Burns et al., EMBO J. 3:2787, 1984).

Over 50 derivatives of butyric acid have since been found to be effective in stimulating fetal globin production (S. P. Perrine et al., Biochem. Biophys. Res. Commun. 148:694–700, 1987). Some of these include butyric acid salts such as sodium and arginine butyrate, α-amino-n-butyric acid (butyramide; $CH_3CH_2CH_2CONH_2$), and isobutyramide ($CH_3CH(CH_3)CONH_2$). Although promising in pilot clinical studies, treated patients were unable to maintain adequate levels of fetal globin in their system. It was later determined that many of these forms of butyric acid had extremely short-half lives. Oxidation in the serum, clearance by hepatocytes and filtration through the kidneys rapidly eliminated these agents from the patient's system. With others, patients rapidly developed tolerance or metabolites of compounds had the opposite desired effect.

A number of aliphatic carboxylic acids have been tested for their ability to specifically increase fetal globin expression in K562 human erythroleukemia cells (S. Safaya et al., Blood 84:3929–35, 1994). Although longer chains were considered toxic to cells, propionate ($CH_3CH_2COOH$) and valerate (pentanoic acid; $CH_3CH_2CH_2CH_2COOH$) were found to be most effective. Butyrate ($CH_3(CH_2)_2COOH$), caproate ($CH_3(CH_2)_4COOH$), caprylate ($CH_3(CH_2)_6COOH$), nonanoate ($CH_3(CH_2)_7COOH$), and caprate ($CH_3(CH_2)_8COOH$) produced much less of an effect. Phenyl acetate ($C_6H_5CH_2COOH$) and its precursor, 4-phenyl butyrate ($C_6H_5CH_2CH_2CH_2COOH$), were found to decrease fetal globin expressing reticulocyte proliferation, but increase relative proportions of fetal globin per cell in cultured erythroid progenitor cells (E. Fibach et al., Blood 82:2203–9, 1993). Acetate ($CH_3COOH$), a metabolic product of butyrate catabolism, increased both erythrocyte precursor populations and also fetal globin synthesis. However, these studies also demonstrated that positive effects could only be maintained for very short periods of time (B. Pace et al., Blood 84:3198–204, 1994).

Other agents shown to affect fetal globin expression include activin and inhibin. Inhibin, a disulfide linked hormone of two subunits, suppresses secretion of follicle-stimulating hormone from the pituitary gland. Activin, sometimes referred to as erythroid differentiating factor (EDF) or follicle-stimulating hormone releasing protein (FRP), is also a hormone and both of these macromolecules induced hemoglobin accumulation in cultured human erythrocytes (S. P. Perrine et al., Blood 74:114a, 1989). Recently, studies have shown that steel factor, a product of the mouse steel locus (D. M. Anderson et al., Cell 63:235–43, 1990), is also capable of influencing fetal globin synthesis in erythroid progenitors (B. A. Miller et al., Blood 79:1861–68, 1992).

Other methods to increase fetal globin expression have focused on recruitment and reprogramming of erythroid progenitor cells to increase total globin expression. For example, the hematopoietic growth factor erythropoietin (EPO) was found to be a potent, although not a fetal-specific, reticulocyte stimulator (Al-Khatti et al., Trans. Assoc. Am. Physicians 101:54, 1988; G. P. Rodgers et al., N. Engl. J. Med. 328:73–80, 1993). In one experiment, animals were treated with EPO following a specific course of therapy (U.S. Pat. No. 4,965,251). According to this experiment, a high dose of erythropoietin was administered in a first time period followed by a second time period wherein erythropoietin was withheld. Following this regimen of treatment, typical for a cytokine, F-reticulocyte colonies cultured from samples obtained from two chronically-anemic baboons increased from 6–8% and 20% pre-treatment to 23% and 50% post-treatment, respectively.

These methods were somewhat advantageous to artificially phlebotomized baboons, but would be entirely counter-productive to patients with a hemoglobinopathy. As thalassemic patients express high levels of EPO, supplemental treatments with EPO would have little to no effect. Sickle cell patients and other patients with unstimulated levels would also not benefit from supplemental EPO treatments because absolute amounts of both $\alpha$-globin and non $\alpha$-globin would increase. Defective non-$\alpha$ globin such as thalassemic forms of $\beta$-globin, would seriously interfere with formation of hemoglobin proteins and, consequently, oxygen transport. Any beneficial effects attributable to increased fetal hemoglobin would be negated as supplemental treatments with EPO would increase both the frequency and number of sickle cell crises, both of which are to be avoided in such patients.

Other hematopoietic growth factors, such as granulocyte/macrophage-colony stimulating factor (GM-CSF) and interleukin 3 (IL-3), were also tested in vivo or in vitro for the ability to stimulate F-reticulocytes (M. Giabbianelli et al., Blood 74:2657, 1989; A. R. Migliaccio et al., Blood 76:1150, 1990). Both of these factors were found to non-specifically increase fetal -globin synthesis in tissue culture cells.

SUMMARY OF THE INVENTION

The invention overcomes the problems and disadvantages associated with current strategies and designs and provides novel compositions and methods for the treatment and prevention of blood disorders.

One embodiment of the invention is directed to methods for the treatment of blood disorders and other maladies such as neoplasia by administering compositions to a patient in pulses. Pulse therapy according to the methods of the invention is much more effective than continuous therapy. The effective dose as well as the total amount of composition needed by the patient to be therapeutically effective is decreased as compared to amounts required for similar effect with continuous therapy. Further, as most chemical compositions are non-toxic at all effective doses, pulsed administration can be continued for very long periods with no adverse effects to the patient.

Another embodiment of the invention is directed to methods for the stimulation of cell proliferation by the administration of erythropoietin or other cell stimulatory agent to a patient and the administration of a chemical composition of the invention in pulses. Such a treatment regimen prepares bone marrow cells for stimulation and increases overall hemoglobin expression and production in the body.

Another embodiment of the invention is directed to novel chemical compounds such as 2,2-dimethyl and 2,2-diethyl butyrate, o-benzoyl lactate, n-dimethylbutyrate glycine amide, o-dimethyl butyrate lactate, 3-phenyl butyrate, 4-chloro-2-phenoxy-2-propionic acid and choline salts of these and other compounds, and to methods for administering these compositions that can be used, either with or without pulsing, for the treatment of blood and other disorders such as neoplasia.

Other objects and advantages of the invention are set forth in part in the description which follows, and in part, will be obvious from this description, or may be learned from the practice of the invention.

DESCRIPTION OF THE INVENTION

Figure 1A:
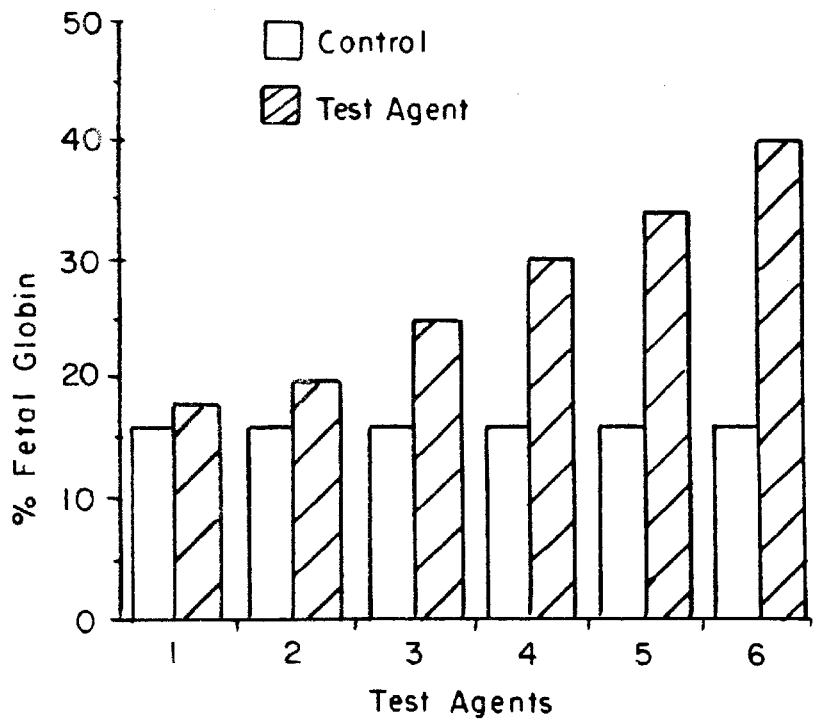
FIG. 1. Comparison of fetal globin produced in (A) normal and (B) sickle cell erythroid progenitor colonies developing in the presence or absence of test compounds.

As embodied and broadly described herein, the present invention is directed to compositions and methods for the administration of pharmaceutical compositions useful for the treatment and prevention of disorders including cell proliferative disorders such as malignancies and cytopenias, and blood disorders such as an anemia, sickle cell syndrome and thalassemia.

Disorders of globin gene expression are extremely varied and produce a wide range of clinical manifestations. Consequences to the individual range from a mild weakness after exertion to a prolonged and protracted series of crises leading to an early death. Increased expression of the hemoglobin macromolecule or specific globin peptide chains has been shown to alleviate many of these manifestations, improving and prolonging the life of the afflicted individual. Some of the more successful treatments involve the administration of biologically active proteins or chemical compounds to promote hematopoiesis, to promote the proliferation of hemoglobin expressing cells or to increase or stimulate the expression of fetal globin protein. Although promising, these treatments have a number of drawbacks. Many substances are carcinogenic or mutagenic and prolonged use would pose serious risks to the patient. Some require continuous use at fairly high doses while others have short effective half-lives. Tolerance to the active ingredient often develops rendering the composition functionally useless. In addition to problems associated with tolerance, the substances themselves or their metabolic by-products or carriers quickly reach toxic levels in the patient's system which slow or inhibit blood cell proliferation. Further, the chemical compounds themselves can be rapidly destroyed by catabolic enzymes, found in the cells and serum such as aminases, oxidases and hydrolases. Many of these enzymes are also found in hepatic cells, the principal sites for cleansing of the blood. Those able to survive cellular and hepatic catabolic processes are quickly eliminated from the patient's system by nephrotic cells of the kidneys. Consequently, in vivo retention times for active compounds are extremely short and the ability to achieve any sort of sustained biological effect becomes nearly impossible or, at least, impractical.

It has been discovered that a variety of chemicals useful for the treatment of blood and other disorders are more effective when administered to a patient in pulses. Pulse therapy is not a form of discontinuous administration of the same amount of a composition over time, but comprises administration of the same dose of the composition at a reduced frequency or administration of reduced doses. This mode of therapy has not been previously reported.

According to these methods, blood and other disorders can be effectively treated and without unnecessary adverse side effects to the patient. Although most compositions are generally safe and non-toxic at therapeutic doses, pulsed administration further reduces risks associated with, for example, toxicity, allergic reactions, the build-up of toxic metabolites and inconveniences associated with conventional treatment. In addition, chemical compositions, being useful at a reduced dose and frequency, have a substantially reduced risk of induced tolerance. Drugs are not inactivated by cellular enzymes or cleared from cells and organs prior to having the desired effect. Further, long-term therapy, typically required for the amelioration of many blood disorders, becomes possible. Consequently, doses necessary for maintaining a constant effect for the patient are steady and material costs and inconveniences associated with administration are substantially reduced.

One embodiment of the invention is directed to the pulsed administration of pharmaceutical compositions for the treatment or prevention of a blood disorder. Pulsed administration is surprisingly more effective than continuous treatment as pulsed doses are often lower than would be expected from continuous administration of the same composition. Each pulse dose can be reduced and the total amount of drug administered over the course of treatment to the patient is minimized.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient drug available for a long period of time. Pulsed administration can substantially reduce the amount of the composition administered to the patient per dose or per total treatment regimen with an increased effectiveness. This represents a significant saving in time, effort and expense and, more importantly, a lower effective dose substantially lessens the number and severity of complications that may be experienced by the patients. As such, pulsing is surprisingly more effective than continuous administration of the same composition.

Preferably, compositions contain chemicals that are substantially non-toxic. Substantially non-toxic means that the composition, although possibly possessing some degree of toxicity, is not harmful to the long-term health of the patient. Although the active component of the composition may not be toxic at required levels, there may also be problems associated with administering the necessary volume or amount of the final form of the composition to the patient. For example, if the composition contains a salt, although the active ingredient may be at a concentration that is safe and effective, there can be a harmful build-up of sodium, potassium or another ion. With a reduced requirement for the composition or at least the active component of that composition, the likelihood of such problems can be reduced or even eliminated. Consequently, although patients may have minor or short term detrimental side-effects, the advantages of taking the composition outweigh the negative consequences.

Methods for the pulsed administration of compositions of the invention are preferably used for the treatment of blood disorders such as hemoglobinopathies (e.g. sickle cell anemia, thalassemia), neoplastic diseases including tumors, leukemias, lymphoproliferative disorders and metastases, and cell proliferative disorders such as viral-induced malignancies (e.g. latent virus infections) and cytopenia including red and white blood cell anemia, leukopenia, neutropenia and thrombocytopenia. Compositions most effective at pulsed administration are typically non-toxic or non-cytotoxic chemicals without any substantial proteinaceous active component at the therapeutically effective pulsed dose. Preferably, treatment does not stimulate apoptosis in the cells being directly treated or in the otherwise normal cells of the body which will also be exposed to the composition.

Individual pulses can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours. Alternatively, periodic doses can be administered in a single bolus or a small number of injections of the composition over a short period of time, typically less than 1 or 2 hours. For example, arginine butyrate has been administered over a period of 4 days with infusions for about 8 hours per day or overnight, followed by a period of 7 days of no treatment.

This has been shown to be an effective regimen for many thalassemic disorders. Fetal hemoglobin levels rise substantially and there is a significant rise in the number of both adult and fetal hemoglobin expressing cells. Substantially means that there are positive consequences that raise the patient's standard of living such as, for example, increased activity or mobility, fewer side-effects, fewer hospital stays or visits to the physician, or fewer transfusions.

The interval between pulses or the interval of no delivery is greater than 24 hours and preferably greater than 48 hours, and can be for even longer such as for 3, 4, 5, 6, 7, 8, 9 or 10 days, two, three or four weeks or even longer. As the results achieved may be surprising, the interval between pulses, when necessary, can be determined by one of ordinary skill in the art. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life. For compositions with fairly rapid half lives such as arginine butyrate with a half-life of 15 minutes, intervals may be 25, 50, 100, 150, 200, 250 300 and even 500 times the half life of the chemical composition.

The number of pulses in a single therapeutic regimen may be as little as two, but is typically from about 5 to 10, 10 to 20, 15 to 30 or more. In fact, patients can receive drugs for life according to the methods of this invention without the problems and inconveniences associated with current therapies. Compositions can be administered by most any means, but are preferable delivered to the patient as an injection (e.g. intravenous, subcutaneous, intraarterial), infusion or instillation, and more preferably by oral ingestion. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Compositions administered in pulses have the surprising benefit of reducing the overall load of drug on the patient as the total amount of drug administered can be substantially less than that amount that has been therapeutically administered by conventional continuous therapy. For example, arginine butyrate has been shown to be effective at continuous administration at about 2000 mg/kg patient weight. Doses of between about 400 to 1500 mg/kg, preferably from about 600 to 1000 mg/kg and more preferably from 700 to 800 mg/kg, when administered in pulses, are surprisingly more beneficial as measured by a rise in fetal hemoglobin levels in thalassemic patients. Typical pulsed amounts of arginine butyrate are from about 2 to about 20 g/kg/month, and preferably from about 3 to about 10 g/kg/month wherein the patient receives a total of less than about 20 kg per month, preferably less than about 15 kg per month and more preferably less than about 10 kg per month. The amounts administered per pulse as well as the total amount of the composition received by the patient over the regimen is substantially reduced. Preferably, the therapeutically effective pulsed dose is less than the continuous dose, or less than one half, one third, one quarter, one fifth, one tenth or even one twentieth of the therapeutic continuous dose of the same composition or even less.

A treatment regimen can be considered effective if it stimulates globin chain expression or the proliferation of erythroblasts or other erythroid progenitor cells, for example with hemoglobinopathy patients, the proliferation of cells such as white blood cells or platelet forming cells, or reduces the number of proliferating cells in, for example, a tumor or other malignancy. Cell numbers are usually most easily determined from peripheral blood sampling or from calculations of tumor size.

Another embodiment of the invention is directed to methods for the pulsed administration of compositions to a patient along with the pulsed or non-pulsed administration of other compositions or therapies for the treatment or amelioration of a disorder. Pulsing of either or both of the compositions can, in part, synchronize cell development, as there is an increased proliferation of erythrocytes and an increased expression of hemoglobin, specifically, fetal hemoglobin. Compositions and therapies which can be pulsed include most of the known or conventional or already well-known treatment regimens. One preferable treatment involves the pulsed or continuous administration of erythropoietin, or another bone marrow cell stimulant, followed by the pulsed administration of a chemical composition of the invention. This regimen has the beneficial effect of stimulating the process of E/Mega cell to erythrocyte development and proliferation which can be followed by stimulation of fetal globin gene expression from the newly proliferated cells. Following such treatments, fetal globin levels in the body rise substantially and much higher than would have been expected from conventional continuous therapy.

A blood disorder is any disease or malady which could be characterized as a direct or indirect consequence of a defect or disease of hemoglobin producing cells or the production of hemoglobin. The blood disorder may be associated with an anemia such as sickle cell anemia, hemolytic anemia, infectious anemia, aplastic anemias, hypoproliferative or hypoplastic anemias, sideroblastic anemias, myelophthisic anemias, antibody-mediated anemias, anemias due to enzyme-deficiencies or chronic diseases, anemias due to blood loss, radiation therapy or chemotherapy, thalassemias including $\alpha$-like and $\beta$-like thalassemias. Treatable blood disorders also include syndromes such as hemoglobin C, D and E disease, hemo-globin lepore disease, and HbH and HbS diseases. Treatment ameliorates one or more symptoms associated with the disorder. Symptoms typically associated with blood disorders include, for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic crises and pain such as angina pectoris.

Compositions to be administered according to the methods of the invention are preferably physiologically stable and safe, and contain one or more chemical compounds that increase the extent or magnitude of hematopoiesis, increase the proliferation of hemoglobin expressing and other cells, increase or balance the expression of globin proteins or increase or stimulate the specific expression of functional globin protein such as $\gamma$-globin. Stimulation of specific gene expression involves activation of transcription or translation promoters or enhancers, or alteration of the methylation pattern or histone distribution along the gene to promote expression. Expression may also be stimulated by inhibition of specific transcription or translation repressors, activation of specific transcription or translation activation factors, or activation of receptors on the surface of particular populations of cells. Stimulation may recruit additional cells to marrow, reprogram differentiated cells to express hemoglobin or switch to the expression of an embryonic, fetal or other globin-like peptide. Stimulation may also activate a previously dormant or relatively inactive genes which substitutes for the defective or damaged gene products such as, for example, the post-natally suppressed genes which encode ε, δ or γ globin, which can substitute for adult β globin, or ζ globin which can substitute for a defective or deficient α globin.

Alternatively, compositions may be used to turn down the expression of those genes whose products are being over expressed and thereby disrupting the balanced production of normal globin proteins. Genes whose expression or whose balanced expression can be effected by the compositions include the globin genes such as the various forms of the ζ-type genes, the ε-type genes, the α-type genes, the -type genes, the δ-type genes, the γ-type genes and at least partially functional pseudo-globin genes.

The mechanism of action of many of the chemical compounds or active ingredients of compositions for the treatment of blood disorders involves effecting one or more of the processes of cell proliferation, cell recruitment, specific hemoglobin expression, heme synthesis or globin chain synthesis. Cell proliferation may be increased, for example, by stimulating stem cells, CFUs, BFUs, megakaryocytes, myeloid cells, platelets, white blood cells or pro-erythrocyte colony growth, or decreased, for example, by effecting a cell's period in or ability to transverse a stage (S, $G_0$, $G_1$, M) of the cell cycle. Cell recruitment may be promoted through the expression of specific cytokines such as cell surface receptors or secreted factors. Hemoglobin expression can be increased or decreased by affecting heme expression, globin peptide expression, heme/globin peptide assembly, globin peptide glycosylation or globin transport through the golgi apparatus. Globin expression can be increased or decreased by altering chromatin and/or nucleosome structure to render a genetic element more or less susceptible to transcription, by altering DNA structure, for example, by methylation of G residues, by affecting the activity of cell-specific transcription or translation factors such as activators or repressors, or by increasing the rate of transcription or translation. For example, useful chemical compounds include phenoxyacetic acid, methoxyacetic acid, butyric acid ethyl ester, cinnamic acid, hydrocinnamic acid, α-methyl cinnamic acid and α-methylhydrocinnamic acid (αMHCA) stimulate alterations in binding or removal of transcription factors from the proximal promoter region of certain genes of the γ- and β-globin gene clusters and thereby increase post-natally suppressed gene expression.

Chemical compounds preferably increase the expression of hemoglobin, increase the expression of one or more embryonic or fetal globin genes or increase the number of hemoglobin expressing or fetal globin expressing reticulocytes. Preferably, compositions increase embryonic or fetal globin gene expression or embryonic or fetal reticulocyte counts greater than about 2%, more preferably greater than about 5%, and even more preferably greater than about 9%. For comparative purposes, a 4% increase in fetal globin gene expression equates to about 20% to 25% rise or increase in fetal globin in peripheral blood samples. Consequently, an increase of greater than about 1% fetal globin expression, preferably greater than about 3%, or about 1% fetal globin expressing cells, preferably greater than about 3%, can alleviate symptoms associated with beta globin disorders.

Hemoglobin expression, globin expression and cell proliferation can be assayed by measuring fold increases in expressed amounts of specific protein or numbers of specific cells in treated samples as compared to untreated controls. Utilizing this criteria, compositions preferably increase the amount of hemoglobin expression, the amount of globin expression, the number of hemoglobin expressing cells or the number of globin expressing cells by greater than or equal to about two-fold, preferably about four-fold and more preferably about eight-fold.

Chemical compounds which perform one or more of these biological functions have the structure $R_1$—$R_2$—$R_3$, preferably $R_1$—C(O)—$R_2$—$R_3$, wherein $R_1$ is $CH_x$, $H_x$, $NH_x$, $OH_x$, $SH_x$, $CONH_x$, COOH, $COSH_x$ or $COH_x$; $R_2$ is $CH_x$ or a branched or linear alkyl chain; $R_3$ is $CH_x$, $H_x$, $NH_x$, $OH_x$, $SH_x$, $CONH_x$, COOH, $COSH_x$, $COOR_4$, $COR_4$ or $OR_4$; $R_4$ is $CH_x$, $H_x$, $NH_x$, $OH_x$, $SH_x$ or a branched or linear alkyl chain; or phenyl-$R_5$—$R_6$—$R_7$ wherein phenyl is a six carbon benzyl or a hydrogenated, hydroxylated or halogenated six carbon ring; $R_5$ is $CH_x$, $NH_x$, $OH_x$ or $SH_x$; $R_6$ is $CH_x$ or a branched or linear alkyl chain; $R_7$ is $CH_x$, $H_x$, $NH_x$, $OH_x$, $SH_x$, $CONH_x$, COOH, $COSH_x$, $COOR_8$, $COR_8$ or $OR_8$; $R_8$ is $CH_x$, $H_x$, $NH_x$, $OH_x$, $SH_x$ or a branched or linear alkyl chain; and x is 0, 1, 2 or 3; or an amine, an amide or a salt thereof. Preferably, $R_2$ comprises between 1 to 8 carbon atoms and more preferably 1, 2, 3 or 4 carbon atoms. Preferably, $R_4$ comprises between 1 to 8 carbon atoms and more preferably 1, 2, 3 or 4 carbon atoms. Preferably, $R_6$ comprises between 1 to 8 carbon atoms and more preferably 1, 2, 3 or 4 carbon atoms. Preferably, $R_8$ comprises between 1 to 8 carbon atoms and more preferably 1, 2, 3 or 4 carbon atoms.

Examples of chemical compounds of the structure $R_1$—$R_2$—$R_3$ or $R_1$—C(O)—$R_2$—$R_3$ include acids, amines, monoamides and diamides of butyric acid ($H_3C$—$CH_2$—$CH_2$—COOH), butyric acid ethyl ester ($CH_3CH_2CH_2COCH_2CH_3$), 4,4,4-trifluorobutyric acid ($CF_3CH_2CH_2COOH$), 2,2-dimettyl butyric acid ($C_2H_5C(CH_3)_2CO_2H$), 2,2-diethyl butyric acid, 3,3-dimethyl butyric acid ($C_6H_{12}O_2$), 3,3-dithyl butyric acid, fumaric acid (HOOCCH=CHCOOH), fumaric acid monomethyl and monoethyl ester, fumaric acid monoamide ($C_4H_5O_2N$), fumaramide ($H_2NCOCHCHCONH_2$), succinic acid ($HOOCCH_2CH_2COOH$) (succinamic acid and succinamide), 2,3-dimethyl succinic acid and methoxy acetic acid ($CH_3CH_2OCH_3$). Examples of chemical compounds of the structure phenyl-$R_5$—$R_6$—$R_7$ include acids, amines and amides of phenoxyacetic acid ($C_6H_5OCH_2COOH$; $C_6H_5OCH_2COONH_3$), 2- and 3-thiophenoxy propionic acid ($C_6H_5SCH(CH_3)COOH$; $C_6H_5SCH_2CH_2COOH$), 2- and 3-phenoxy propionic acid ($C_6H_5OCH(CH_3)COOH$; $C_6H_5OCH_2CH_2COOH$), 2- and 3-phenyl propion ($C_6H_5CH(CH_3)COOH$; $C_6H_5CH_2CH_2COOH$), 4-chlorophenoxy-2-propionic acid ($ClC_6OCH_2CH_2CO_2H$), methoxy acetic acid ($H_3COCH_2CO_2H$), and 2-thiophenoxy acetic acid ($C_6H_5SCH_2COOH$). Examples of chemical compounds of the structure phenyl-$R_9$—$R_{10}$ include acids, amines and amides of cinnamic acid ($C_6H_5CH$=CHCOOH), hydrocinnamic acid, dihydro cinnamic acid ($C_6H_5CH_2CH_2COOH$), α-methyl hydrocinnamic acid or dihydrocinnamic acid, 2,3-dimethyl hydrocinnamic or dihydrocinnainic acid, phenyl acetate ethyl ester ($C_6H_5CH(CH_3)CH_2COCH_2CH_3$), 2-phenoxypropionic acid ($C_6H_5OCH_2CO_2H$), phenoxy acetic acid ($CH_3CH(OC_6H_5)CO2H$), and 3-phenyl butyric acid ($C_6H_5CH(CH_3)CH_2COOH$). Additional chemical compounds which may or may not be included in the above classification scheme include monobutyrin, tributyrin ($CH_2(OCOCH_2CH_2CH_3)CH_2(OCOCH_2CH_2CH_3)CH_2(OCOCH_2CH_2CH_3)$), ethyl-phenyl acetic acid ($CH_3CH_2C_6H_5CH_2COOH$), indol-3-propionic acid, indol-3-butyric acid, 1- and 2-methyl cyclopropane carboxylic acid ($C_5H_8O_2$ and $C_6H_8O_2$), mercaptoacetic acid ($C_2H_4O_2S$), ($ClCH_2CH_2CO_2H$), 3-trimethyl silyl-1-proposulfonic acid sodium ($C_6H_{15}O_3SS$), 2-oxopantansane ($C_5H_8O_3$), isobutly hydroxylamine HCl ($C_4H_{12}OCl$), 2-methyl butanoic acid ($C_5H_{10}O_2$), o-benzoyl lactate, n-dimethylbutyric acid glycine amide, o-dimethyl butyric acid lactate, and diethyl butyric acid.

One preferred class of compounds includes $C_{1-12}$-yl hydroxamates, more preferably $C_{1-6}$, such as propionyl hydroxamate and butyryl hydroxamate, $C_{1-12}$ hydroxamic acids, and $C_{1-12}$ bis hydroxamic acids, such as superoyl bis hydroxamic acid. Particularly prefered compounds are propionyl hydroxamate, butyryl hydroxamate, and superoyl bis hydroxamic acid. These compounds show an increase in growth proliferation of cells at micromolar concentrations, such as an increase in percentage γ globin (fetal) in cell cultures from 1- to 10-fold at micromolar concentrations compared to untreated erythroid cells. For a therapeutic compound to ameliorate clinical symptoms in the β-hemoglobinopathies and β-thalassemias, induction of fetal globin expression (or synthesis) by as little as 8% in the bone marrow (or reticulocytes) can result in 3-fold more fetal hemoglobin in the peripheral blood of a patient. This 3-fold increase is typically seen due to selective survival of the red blood cells which express or contain fetal globin, compared to underlying red blood cells which have only abnormal or deficient globin, and typically only survive for hours to days in β-thalassemia patients and for 2 weeks in sickle cell patients (rather than for 4 months in normal individuals).

Chemical compounds are preferably optically pure with a specific conformation (plus {+} or minus {−}), absolute configuration (R or S), or relative configuration (D or L). Particular salts such as sodium, potassium, magnesium, calcium, choline, amino acid, ammonium or lithium, or combinations of salts may also be preferred, however, certain salts may be more advantageous than others. For example, chemical compounds that require high doses may introduce too much of a single salt to the patient. Sodium is generally an undesirable salt because at high doses, sodium can increase fluid retention resulting in tissue destruction. In such instances, combinations of different salts or alternative salts can be used.

In addition to the above chemical compounds, other compounds include derivatives of these chemicals. Derivatives are chemical or biological modifications of the parent compound and include analogs, homologs, next adjacent homologs and compounds based on any of the foregoing. Analogs include both structural and functional analogs. Functional analogs are those compounds which are functionally related to the activity of the parent compound. Structural analogs are those compounds related to the parent compound in the arrangement or number of carbon atoms. For example, such compounds may have double or triple covalent bonds wherein the parent has a single covalent bond. Homologs are those compounds which have the same number of carbon atoms as the parent compound, but further comprise additional moieties such as one or more phosphate groups ($PO_4$), sulfate groups ($SO_3$), amines and amides ($NH_3$), nitrate groups ($NO_2$), acidified or esterified carbon atoms or combinations thereof. Next adjacent homologs are those compounds with one more or less carbon atom. Related compounds include those compounds which have been modified such as by substitutions and/or additions. For example, compounds of the invention may be substituted with one or more halogens such as chlorine (Cl), fluorine (F), iodine (I), bromine (Br) or combinations of these halogens. As known to those of ordinary skill in the art, halogenation can increase the polarity, hydrophilicity or lipophilicity or a chemical compound which can be a desirable feature, for example, to transform a chemical compound into a composition which is more easily tolerated by the patient or more readily absorbed by the epithelial lining of the gastrointestinal tract. Such compositions could be orally administered to patients.

Therapeutically effective chemical compounds may be created by modifying any of the above chemical compounds so that after introduction into the patient, these compounds metabolize into active forms, such as the forms above, which have the desired effect on the patient. Compounds may also be created which are metabolized in a timed-release fashion allowing for a minimal number of introductions which are efficacious for longer periods of time. Combinations of chemical compounds can also produce useful new compounds from the interaction of the combination. Such compounds may also produce a synergistic effect when used in combination with other known or other compounds.

Compositions may also comprise proteinaceous agents such as cytokines that will increase the extent or magnitude of hematopoiesis, increase the proliferation of hemoglobin expressing cells, increase or balance the expression of hemoglobin macromolecules or increase or stimulate the specific expression of alternate globin genes such as γ-globin. Such proteinaceous agents include steel factor, insulin, erythropoietin (EPO), interferon (IFN), insulin growth factor (IGF), stem cell factor (SCF), macrophage-colony stimulating factor (M-CSF), granulocyte-colony stimulating factor (G-CSF), GM-CSF, growth factors such as fibroblast-derived growth factor (FGF), epidermal growth factor (EGF) and platelet-derived growth factor (PDGF), nerve growth factor (NGF), vascular endothelial growth factor (VEGF), bone morphogenic proteins (BMPs), the interleukins (IL) IL-1, IL-2, IL-3, IL-4, IL-5, IL-6, IL-7, IL-8, etc., activin also referred to as erythroid differentiation factor (EDF) or follicle-stimulating hormone releasing protein (FRP), inhibin, stem cell proliferation factor (SCPF) and active fragments, subunits, derivatives and combinations of these proteins. Erythropoietin, activin and SCF all stimulate the proliferation of stem cells, committed cells and erythroid progenitor cells, and can also stimulate the expression of embryonic globin, fetal globin or partly functional pseudo-globin expression. The hematopoietic factor, steel factor, also referred to as kit ligand, mast cell growth factor and stem cell factor, recruits and stimulates the proliferation of hemoglobin expressing cells and the specific expression of embryonic or fetal globin. Proteinaceous agents of the invention may also be aminated, glycosylated, acylated, neutralized, phosphorylated or otherwise derivatized to form compositions which are more suitable for the method of administration to the patient or for increased stability during shipping or storage.

Compositions may be physiologically stable at therapeutically effective concentrations. Physiological stable compounds are compounds that do not break down or otherwise become ineffective upon introduction to a patient prior to having a desired effect. Compounds are structurally resistant to catabolism, and thus, physiologically stable, or coupled by electrostatic or covalent bonds to specific reagents to increase physiological stability. Such reagents include amino acids such as arginine, glycine, alanine, asparagine, glutamine, histidine or lysine, nucleic acids including nucleosides or nucleotides, or substituents such as carbohydrates, saccharides and polysaccharides, lipids, fatty acids, proteins, or protein fragments. Useful coupling partners include, for example, glycol such as polyethylene glycol, glucose, glycerol, glycerin and other related substances.

Physiological stability can be measured from a number of parameters such as the half-life of the compound or the half-life of active metabolic products derived from the compound. Certain compounds of the invention have in vivo half lives of greater than about fifteen minutes, preferably greater than about one hour, more preferably greater than about two hours, and even more preferably greater than about four hours, eight hours, twelve hours or longer. Although a compound is stable using this criteria, physiological stability can also be measured by observing the duration of biological effects on the patient. These effects include amelioration or elimination of patient symptoms, an increase in number or appearance of hemoglobin producing cells, or an alteration, activation or suppression of specific gene expression, such as, for example, the persistence of fetal globin chain expression in blood cells.

Symptoms may be clinically observed or biologically quantified. For example, observed symptoms are those which can be clinically perceived and include pathological alterations in cellular morphology such as red cell sickling, anemic crises, jaundice, splenomegaly, hepatomegaly, hemorrhaging, tissue damage due to hypoxia, organ dysfunction, pain such as angina pectoris, fatigue including shortness of breath, weakness and poor exercise ability, and pallor. Clinical symptoms which are important from the patient's perspective include a reduced frequency or duration, or elimination of the need for transfusions or chelation therapy. Quantifiable biological symptoms are those which can be more accurately measured such as anemia, enzyme activity, hematocrit and hemoglobin levels, decreased cell viability, ineffective erythropoiesis, abnormal reticulocyte count, abnormal iron loads, inadequate peripheral blood flow, anuria, dyspnea, hemolysis and specific gene expression. Other quantifiable biological activities include, for example, the ability to recruit and stimulate the proliferation of hemoglobin expressing cells, the ability to increase hemoglobin expression, the ability to balance α-type and β-type globin gene expression or the ability to increase expression of embryonic, fetal or at least partially functional pseudo-globin genes. Preferably, a stable compound of the invention has an in vivo half-life of greater than about 15 minutes, a serum half-life of greater than about 15 minutes, or a biological effect which continues for greater than 15 minutes after treatment has been terminated or the serum level of the compound has decreased by more than half.

Compositions are not significantly biotransformed, degraded or excreted by catabolic processes associated with metabolism. Although there may be some biotransformation, degradation or excretion, these function are not significant if the composition is able to exert its desired effect. Catabolic processes include deamination of aminases, hydrolysis of esters and amides, conjugation reactions with, for example, glycine or sulfate, oxidation by the cytochrome p450 oxidation/reduction enzyme system and degradation in the fatty acid pathway. Hydrolysis reactions occur mainly in the liver and plasma by a variety of non-specific hydrolases and esterases. Both deaminases and amidases, also localized in the liver and serum, carry out a large part of the catabolic process. Reduction reactions occur mainly intracellularly in the endoplasmic reticulum and transferases perform conjugation reactions mainly in the kidneys and liver.

Compositions are also preferably safe at effective dosages. Safe compositions are compositions that are not substantially toxic (e.g. cytotoxic or myelotoxic), or mutagenic at required dosages, do not cause adverse reactions or side effects, and are well tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures and other central nervous system difficulties, fever, bleeding or hemorrhaging, serum abnormalities and respiratory difficulties.

Compositions useful for treating blood disorders preferably do not substantially affect the viability of a cell such as a normal mammalian cell, the cell being treated or effected by the chemical compound. Normal cell viability, the viability of an untransformed or uninfected cell, can be determined from analyzing the effects of the composition on one or more biological processes of the cell. Detrimental interference with one or more of these cellular processes becomes significant when the process becomes abnormal. Examples of quantitatable and qualifiable biological processes include the processes of cell division, protein synthesis, nucleic acid (DNA or RNA) synthesis, nucleic acid (principally DNA) fragmentation and apoptosis. Others processes include specific enzyme activities, the activities of the cellular transportation systems such as the transportation of amino acids by system A (neutral), system B (acidic) or system C (basic), and the expression of a cell surface protein. Each of these parameters is easily determined as significantly detrimental, for example, in tissue culture experiments, in animal experiments or in clinical studies using techniques known to those of ordinary skill in the art. Abnormal cell division, for example, can be mitosis which occurs too rapidly, as in a malignancy, or unstably, resulting in programmed cell death or apoptosis, detected by increased DNA degradation. The determination of abnormal cell viability can be made on comparison with untreated control cells. Compositions preferably increase normal cell viability. Increased cell viability can be determined by those of ordinary skill in the art using, for example, DNA fragmentation analysis. A decreased amount of fragmentation indicates that cellular viability is boosted. Determinations of increased or decreased viability can also be concluded from an analysis of the results of multiple different assays. Where multiple tests provide conflicting results, accurate conclusions can still be drawn by those of ordinary skill based upon the cell type, the correctness or correlation of the tests with actual conditions and the type of composition.

Compositions can be prepared in solution as a dispersion, mixture, liquid, spray, capsule or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil or a relatively inert solid or liquid. Liquids administered orally may include flavoring agents such as mint, cherry, guava, citrus, cinnamon, orange, mango, or mixed fruit flavors to increase palatability. Pills, capsules or tablets administered orally may also include flavoring agents. Additionally, all compositions may further comprise agents to increase shelf-life, such as preservatives, anti-oxidants and other components necessary and suitable for manufacture and distribution of the composition. Compositions further comprise a pharmaceutically acceptable carrier. Carriers are chemical or multi-chemical compounds that do not significantly alter or effect the active ingredients of the compositions. Examples include water, alcohols such as glycerol and polyethylene glycol, glycerin, oils, salts such as sodium, potassium, magnesium and ammonium, fatty acids, saccharides or polysaccharides. Carriers may be single substances or chemical or physical combinations of these substances.

Another embodiment of the invention is directed to combinations of compositions comprising a chemical compound in combination with an agent known to positively affect hemoglobin expression or hemoglobin expressing cells. The agent may be a chemical compound such as acetic acid, butyric acid, D- or L-amino-n-butyric acid, α- or β-amino-n-butyric acid, arginine butyrate or isobutyramide, all disclosed in U.S. Pat. Nos. 4,822,821 and 5,025,029. Others include butyrin, 4-phenyl butyrate ($C_6H_5CH_2CH_2CH_2COOH$), phenylacetate ($C_6H_5CH_2COOH$), phenoxy acetic acid, all of which and more are disclosed in U.S. Pat. No. 4,704,402, and U.S. patent application Ser. No. 08/398,588 (entitled "Compositions for the Treatment of Blood Disorders" filed Mar. 3, 1995), and derivatives, salts and combination of these agents. Alternatively, the agent may be a hematopoietic protein such as erythropoietin, steel factor, insulin, an interleukin, a growth factor, hormones such as activin or inhibin, disclosed in U.S. Pat. Nos. 5,032,507 and 4,997,815, and active fragments and combinations of these proteins either with each other or with other chemical compounds. Such composition may have additive or synergistic effects.

Another embodiment of the invention is directed to methods for the treatment of patients with blood disorder comprising the pulsed administration of one or more compositions. Compositions to be administered contain a therapeutically effective pulsed amount of a chemical compound or proteinaceous agent. A therapeutical effective pulsed amount is that amount which has a beneficial effect to the patient by alleviating one or more symptoms of the disorder or simply reduce premature mortality. For example, a beneficial effect may be a decrease in pain, a decrease in duration, frequency or intensity of crises, an increased hematocrit, an improved erythropoiesis, a reduced or eliminated necessity for chelation therapy, an increased reticulocyte count, an increased peripheral blood flow, a decreased hemolysis, decreased fatigue or an increased strength. Preferably, a therapeutic amount is that amount of chemical compound or agent that stimulates or enhances the expression of non-adult globin such as embryonic or fetal globin, or the proliferation of embryonic, fetal or adult globin expressing cells. A therapeutically effective amount for continuous therapy is typically greater than a therapeutically amount that is effective in pulsed therapy. Consequently, pulsed therapy exposes the patient to lower levels of the composition and/or the active ingredient than would be needed with non-pulse therapy.

Compositions provided to the patient may include any combination of the proteins or chemical compounds described herein or known to those of ordinary skill in the art. The patient may be a domesticated animal such as a dog, cat, horse, cow, steer, pig, sheep, goat or chicken, or a wild animal, but is preferably a human or another primate. Administration may be to an adult, an adolescent, a child, a toddler, a neonate or an infant, or administered in utero. Administration of the composition may be short term, continuous or sporadic as necessary. Patients with a suspected or diagnosed with a blood disorder may only require composition treatment for short periods of time or until symptoms have abated or have been effectively eliminated.

Compositions can be directly or indirectly administered to the patient. Indirect administration is performed, for example, by administering the composition to cells ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Direct administration of a composition may be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intra peritoneal injection or direct injection or other administration to one or more specific sites. Injectable forms of administration are sometimes preferred for maximal effect in, for example, bone marrow. When long term administration by injection is necessary, venous access devices such as medi-ports, in-dwelling catheters, or automatic pumping mechanisms are also preferred wherein direct and immediate access is provided to the arteries in and around the heart and other major organs and organ systems.

Another effective method of administering the composition is by transdermal transfusion such as with a dermal or cutaneous patch, by direct contact with, for example, bone marrow through an incision or some other artificial opening into the body. Compositions may also be administered to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral, enema, suppository, or injectable forms of administration. Compositions may be administered as a bolus injection or spray. Compositions that may or may not be pulsed may be given sequentially over time (episodically) such as every two, four, six or eight hours, every day (QD) or every other day (QOD), or over longer periods of time such as weeks to months. Compositions may also be administered in a timed-release fashion such as by using slow-release resins and other timed or delayed release materials and devices.

Orally active compositions are more preferred as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or by modifying the compound with a neutralizing chemical group. Oral bioavailability is also a problem because drugs are exposed to the extremes of gastric pH and gastric enzymes. These problems can be overcome in a similar manner by modifying the molecular structure to withstand very low pH conditions and resist the enzymes of the gastric mucosa such as by neutralizing an ionic group, by covalently bonding an ionic interaction, or by stabilizing or removing a disulfide bond or other relatively labile bond.

Treatments to the patient may be therapeutic or prophylactic. Therapeutic treatment involves administration of one or more compositions of the invention to a patient suffering from one or more symptoms of the disorder. Symptoms typically associated with blood disorders include, for example, anemia, tissue hypoxia, organ dysfunction, abnormal hematocrit values, ineffective erythropoiesis, abnormal reticulocyte count, abnormal iron load, splenomegaly, hepatomegaly, impaired peripheral blood flow, dyspnea, increased hemolysis, jaundice, anemic crises and pain such as angina pectoris. Relief and even partial relief from one or more of these symptoms corresponds to an increased life span or simply an increased quality of life. Further, treatments that alleviate a pathological symptom can allow for other treatments to be administered.

Prophylactic treatments involve pulsed administration of a composition to a patient having a confirmed or suspected blood disorder without having any overt symptoms. For example, otherwise healthy patients who have been genetically screened and determined to be at high risk for the future development of a blood disorder may be administered compositions of the invention prophylactically. Administration can begin at birth and continue, if necessary, for life. Both prophylactic and therapeutic uses are readily acceptable because these compounds are generally safe and non-toxic.

Another embodiment of the invention is directed to a method for regulating the expression of a globin gene in a mammalian cell. Briefly, the cell is exposed to an effective amount of a composition. A poorly expressed or quiescent globin gene of the cell is stimulated to increase the expression of its protein product. An effective amount of the composition is that amount which increases the extent or magnitude of hematopoiesis, increases the proliferation of hemoglobin expressing cells, increases, decreases or balances expression from one or more globin genes, or increases or stimulates the specific expression of one or more globin genes such as an alpha ($\alpha$) globin gene, a zeta ($\zeta$) globin gene, an epsilon ($\epsilon$) globin gene, a beta ($\beta$) globin gene, a delta ($\delta$) globin gene, a gamma (G-$\gamma$ or A-$\gamma$) globin gene, or an, at least, partly functional pseudo-globin gene. Cells can be treated in culture or in vivo. Cultures of treated cells will produce increased amounts of hemoglobin and preferably embryonic or fetal globin. This hemoglobin can be harvested for introduction to a patient or the stimulated cells themselves can be administered to the patient. Alternatively, recombinant cells containing a globin gene which can be stimulated by compositions of the invention can be utilized. These recombinant cells may be heterologous or homologous natural cells, or synthetically created cells such as a lipid vesicles.

Another embodiment of the invention is directed to a method for regulating the proliferation of red blood cells and, preferably, specifically regulating the expression of fetal hemoglobin. As above, an effective amount of a composition is administered in pulses to, for example, a cell population obtained from stem cells, bone marrow, cord blood, yolk sac cells, or fetal cells such as fetal liver cells, or combinations thereof, ex vivo. The pulse-treated cells, or purified products harvested from these cells, are then administered to a patient in vivo. This method can be utilized to treat blood disorders in patients by increasing the amount of one or more different types of globin or hemoglobin expressing cells can alleviate symptoms associated with a blood disorder. Cells can be obtained from volunteers or the patients to be treated. Alternatively, treated cells or products derived from treated cells can be harvested, purified by, for example, column chromatography, and utilized for other medical applications such as diagnostic or other treatment monitoring screening kits.

Another embodiment of the invention is directed to a method for ameliorating a blood disorder by administering a therapeutically effective amount of a pharmaceutical composition containing an agent that stimulates the expression of a globin gene or stimulates the proliferation of hemoglobin expressing cells wherein the composition does not significantly decrease viability of the cell being treated or a normal cell. The therapeutically effective amount is that amount which ameliorates one or more symptoms of the blood disorder or reduces premature mortality. A normal cell is a relatively healthy mammalian cell that is not otherwise infected or transformed. Viability can be assayed by determining the effect of the composition on cell division, protein or nucleic acid synthesis, biochemical salvage pathways, amino acid or nucleotide transport processes, nucleic acid fragmentation or apoptosis and comparing the effects observed to control cells. Pulsing, according to the described treatment regimens, can also be used to administer these and other compositions of the invention and their effects tested in tissue culture, in vivo or by cell counting.

Patients with blood disorders are typically quite infirm with, for example, iron damaged organs and systems. Most treatments further tax the patient's already frail health in an effort to combat the disorder. This is true for both arginine butyrate and isobutyramide which decrease cell viability as determined in DNA fragmentation assays. To decrease cell viability is not desired for the treatment of blood disorders and may even be harmful. Surprisingly, many of the pulsed compositions maintain or, preferably, increase cell viability. This is a great benefit in the treatment of blood disorders and can significantly increase the chances for a successful outcome for the patient. For example, the pulsed administration of phenoxyacetic acid or butyric acid ethyl ester both reduce DNA fragmentation in fragmentation assays, and phenoxyacetic acid and $\alpha$-methyl hydrocinnamic acid do not significantly alter system A transport of amino acids.

As such, pulsed composition can be used to treat or prevent iron overloaded or iron deficient systems such as occurs in transfused patients and anemic patients with thalassemia or sickle cell anemia. As chemicals of the compositions of the invention regulate systems that exploit iron, the amount of free and the amount of available iron in a patient's system can be regulated and carefully controlled. Chelation therapy, often the only conventional treatment available for iron over-loaded transfusion patients, may be lessened or avoided entirely. As chelation therapy is often uncertain and with some risk of its own, the long-term prognosis for these patients is greatly improved.

Another embodiment of the invention is directed to a method for increasing fetal hemoglobin comprising the pulsed administration of a composition to a patient. For example, hemoglobin F content of blood so treated is increased greater than about 2%, preferably greater than about 5% and more preferably greater than about 10%. Patients which can be treated include any mammal such as a human. Chemical compounds which could be utilized include phenoxy acetic acid, butyric acid ethyl ester, cinnamic acid, hydrocinnamic acid, $\alpha$-methyl hydrocinnamic acid, methoxy acetic acid, 2,2-dimethylbutyric acid, 2,2-diethylbutyric acid, phenyl butyric acid, thiophenoxy acetic acid, phenoxy propionic acid, succinamide, or a derivative or modification thereof. Such methods are useful to treat or prevent blood disorders in the same or a different patient. For example, to treat the same patient, the compound can be pulse administered for a therapeutically effective period of time to allow the hemoglobin content of just the globin protein content to rise. Alternatively, the patient can be treated and the patient's blood collected at peak times of hemoglobin or globin production, collected and stored, and administered to another patient or re-administered to the same patient. Such treatments would be useful therapies for those being treated with radiation therapy, chemotherapy, bone marrow transplants, blood diseases, such as sickle cell disease and thalassemia, and other disorders which would be alleviated with an increased blood hemoglobin content.

Another embodiment of the invention is directed to methods for the treatment of a patient with an infection or a neoplastic disorder comprising the pulsed administration of a therapeutically effective composition. Treatable infectious diseases include bacterial infections such as sepsis and pneumonia, infections caused by bacterial pathogens such as, for example, Pneumococci, Streptococci, Staphylococci, Neisseria, Chlamydia, Mycobacteria, Actinomycetes and the enteric microorganisms such as enteric Bacilli; viral infections caused by, for example, a hepatitis virus, a retrovirus such as HIV, an influenza virus, a papilloma virus, a herpes virus (HSV I, HSV II, EBV), a polyoma virus, a slow virus, paramyxovirus and corona virus; parasitic diseases such as, for example, malaria, trypanosomiasis, leishmania, amebiasis, toxoplasmosis, sarcocystis, pneumocystis, schistosomiasis and elephantitis; and fungal infections such as candidiasis, phaeohyphomycosis, aspergillosis, mucormycosis, cryptococcosis, blastomycos is, paracoccidiodomycosis, coccidioidomycosis, histomycosis, actinomycosis, nocardiosis and the Dematiaceous fungal infections.

Anti-neoplastic activity includes, for example, the ability to induce the differentiation of transformed cells including cells which comprise leukemias, lymphomas, sarcomas, neural cell tumors, carcinomas including the squamous cell carcinomas, seminomas, melanomas, neuroblastomas, mixed cell tumors, germ cell tumors, undifferentiated tumors, neoplasm due to infection (e.g. viral infections such as a human papilloma virus, herpes viruses including Herpes Simplex virus type I or II or Epstein-Barr virus, a hepatitis virus, a human T cell leukemia virus (HTLV) or another retrovirus) and other malignancies. Upon differentiation, these cells lose their aggressive nature, no longer metastasize, are no longer proliferating and eventually die and/or are removed by the T cells, natural killer cells and macrophages of the patient's immune system. The process of cellular differentiation is stimulated or turned on by, for example, the stimulation and/or inhibition of gene specific transcription. Certain gene products are directly involved in cellular differentiation and can transform an actively dividing cell into a cell which has lost or has a decreased ability to proliferate. An associated change of the pattern of cellular gene expression can be observed. To control this process includes the ability to reverse a malignancy. Genes whose transcriptional regulation are altered in the presence of compositions of the invention include the oncogenes myc, ras, myb, jun, fos, abl and src. The activities of these gene products as well as the activities of other oncogenes are described in J. D. Slamon et al. (Science 224:256–62, 1984).

Another example of anti-neoplastic activity includes the ability to regulate the life cycle of the cell, the ability to repress angiogenesis or tissue regeneration through the blockade or suppression of factor activity, production or release, the ability to regulate transcription or translation, or the ability to modulate transcription of genes under angiogenesis, growth factor or hormonal control. These activities are an effective therapy particularly against prostatic neoplasia and breast carcinomas. Additional anti-neoplastic activities include the ability to regulate the cell cycle for example by effecting time in and passage through S phase, M phase, $G_1$ phase or $G_0$ phase, the ability to increase intracellular cAMP levels, the ability to inhibit or stimulate histone acetylation, the ability to methylate nucleic acids and the ability to maintain or increase intracellular concentrations of anti-neoplastic agents.

The neoplastic disorder may be any disease or malady which could be characterized as a neoplasm, a tumor, a malignancy, a cancer or a disease which results in a relatively autonomous. growth of cells. Neoplastic disorders prophylactically or therapeutically treatable with compositions of the invention include small cell lung cancers and other lung cancers, rhabdomyosarcomas, chorio carcinomas, glioblastoma multiformas (brain tumors), bowel and gastric carcinomas, leukemias, ovarian cancers, prostate cancers, osteosarcomas or cancers which have metastasized. Diseases of the immune system which are treatable by these compositions include the non-Hodgkin's lymphomas including the follicular lymphomas, Burkitt's lymphoma, adult T-cell leukemias and lymphomas, hairy-cell leukemia, acute myelogenous, lymphoblastic or other leukemias, chronic myelogenous leukemia, and myelodysplastic syndromes. Additional diseases treatable by the compositions include virally-induced cancers wherein the viral agent is EBV, HPV, HIV, CMV, HTLV-1 or HBV, breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas and adenocarcinomas.

In another embodiment of the invention, compositions may be pulse administered in combination with other anti-neoplastic agents or therapies to maximize the effect of the compositions in an additive or synergistic manner. Cytokines which may be effective in combination with the compositions include growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), platelet derived growth factor (PDGF) nerve growth factor (NGF), stem cell factor (SCF), and transforming growth factor (TGF). These growth factors plus a composition may further stimulate cellular differentiation and/or the expression of certain MHC antigens or tumor specific antigens. For example, BCGF plus a composition may be effective in treating certain B cell leukemias. NGF plus a composition may be useful in treating certain neuroblastomas and/or nerve cell tumors. In a similar fashion, other agents such as differentiating agents may be useful in combination with a composition to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

Alternatively, other cytokines and related antigens in combination with a composition may also be useful to treat or prevent neoplasia. Potentially useful cytokines include tumor necrosis factor (TNF), the interleukins (IL-1, IL-2, IL-3, etc.), the interferon proteins (IFN) IFN-α, IFN-β, and IFN-γ, cyclic AMP including dibutyryl cyclic AMP, hemin, hydroxyurea, hypoxanthine, glucocorticoid hormones, dimethyl sulfoxide (DMSO), and cytosine arabinoside, and anti-virals such as acyclovir and gemciclovirs. Therapies using combinations of these agents would be safe and effective against malignancies and other forms of cancer. Combinations of therapies may also be effective in inducing regression or elimination of a tumor or some other form of cancer such as pulsed compositions plus radiation therapy, toxin or drug conjugated antibody therapy using monoclonal or polyclonal antibodies directed against the transformed cells, gene therapy or specific anti-sense therapy. Effects may be additive, logarithmic, or synergistic, and methods involving combinations of therapies may be simultaneous protocols, intermittent protocols or protocols which are empirically determined.

Another embodiment of the invention comprises methods for the pulse administration of compositions for the treatment of neoplastic disorders by augmenting conventional chemotherapy, radiation therapy, antibody therapy, and other forms of therapy. Compositions containing chemical compounds in combination with chemotherapeutic agents, enhance the effect of the chemotherapeutic agent alone. Compositions decrease the expression or activity of proteins responsible for lowering the intra-cellular concentration of chemotherapeutic agents. Proteins responsible for resistance to drugs and other agents, the multi-drug resistance (MDR) proteins, include the P-glycoprotein (Pgp) encoded by the mdr-1 gene. Consequently, conventional drugs for the treatment of neoplastic disorders accumulate at higher concentrations for longer periods of time and are more effective when used in combination with the compositions herein. Some conventional chemotherapeutic agents which would be useful in combination therapy with compositions of the invention include the cyclophosphamide such as alkylating agents, the purine and pyrimidine analogs such as mercaptopurine, the vinca and vinca-like alkaloids, the etoposides or etoposide like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as antiinsulin and antiandrogen, the antiestrogens such as tamoxifen an other agents such as doxorubicin, L-asparaginase, dacarbazine (DTIC), amsacrine (mAMSA), procarbazine, hexamethylmelamine, and mitoxantrone. The chemotherapeutic agent could be given simultaneously with the compounds of the invention or alternately as defined by a protocol designed to maximize drug effectiveness, but minimize toxicity to the patient's body.

Another embodiment of the invention is directed to aids for the treatment of human disorders such as infections, neoplastic disorders and blood disorders. Aids contain compositions of the invention in predetermined amounts which can be individualized in concentration or dose for a particular patient. Compositions, which may be liquids or solids, are placed into reservoirs or temporary storage areas within the aid. At predetermined intervals, a set amount of one or more compositions are administered to the patient. Compositions to be injected may be administered through, for example, mediports or in-dwelling catheters. Aids may further comprise mechanical controls or electrical controls devices, such as a programmable computer or computer chip, to regulate the quantity or frequency of administration to patients. Examples include both single and dual rate infusers and programmable infusers. Delivery of the composition may also be continuous for a set period of time. Aids may be fixed or portable, allowing the patient as much freedom as possible.

The following examples are offered to illustrate embodiments of the present invention, but should not be viewed as limiting the scope of the invention.

EXAMPLES

Example 1

Fetal Globin Production in Erythroid Progenitor Cells.

Fetal globin production was determined in erythroid progenitor cells cultured in the presence or absence of six test compositions (FIG. 1A). Blood was obtained from a normal individual and erythroid cells, purified and plated semi-solid medium containing the chemical compositions (lane 1) α-methyl-cinnamic acid; (lane 2) 3-phenylbutyrate; (lane 3) α-methylhydrocinnamic acid; (lane 4) 2,2-dimethylbutyric acid; (lane 5) phenoxyacetic acid; and (lane 6) thiophenoxyacetic acid. All test compositions were at a concentration of 0.2 mm and cultures were incubated for 10–14 days. As cultures were grown on semi-solid medium, neither the test composition or culture medium was replenished over time.

Proliferation of erythroid colonies (Bfu-e or CFU-e) is believed to be maximal in the presence of IL-3, SCF and EPO. Colonies from samples treated with growth factors alone (GM-CSF, SCF, EPO, IL-6, transferrin, insulin and IGF-1) are shown in white. Dark shaded bars 1–6 represent fetal globin produced in Bfu-e, treated with the respective composition in addition to the panel of maximal growth factors. Significant increases in fetal globin were observed with five of the six compositions tested ($p<0.05$ paired t-test). Absolute levels of 16% γ-glonin (non- c globin) were observed in the controls, while 20–40% γ-globin (non-α globin) was expressed in Bfu-e cultured with the last five compounds.

Figure 1B:
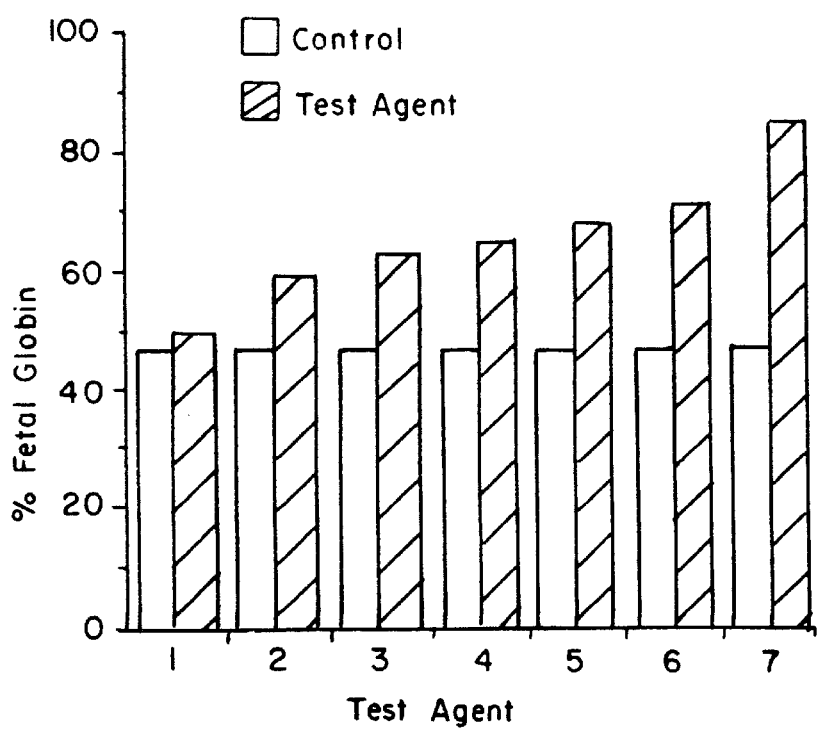

Another experiment was performed using blood samples obtained from a patient with sickle cell anemia and seven different composition were tested and shown in FIG. 1B: (lane 1) methoxyacetic acid; (lane 2) α-methylcinnamic acid; (lane 3) α-methylhydrocinnamic acid; (lane 4) 3-phenylbutyrate; (lane 5) 2,2-dimethylbutyrate; (lane 6); and (lane 7) thiophenoxyacetic acid. As shown, similar results were obtained. Increases in fetal globin were observed with all of the compositions tested ($p<0.05$ paired t-test). Absolute levels of 48% of non-α globin were observed in the controls, while 51% to 83% of non-α globin was expressed in Bfu-e cultured with the compositions. Specifically, methoxyacetic acid showed a marginal 3% increase over controls; α-methylcinnamic acid showed a 12% increase over controls; α-methylhydro cinnamic acid produced an 18% increase over controls; 3-phenylbutyrate produced a 21% increase over controls; 2,2-dimethylbutyrate produced a 24% increase over controls; phenoxyacetic acid produced a 34% increase over controls; and thiophenoxyacetic acid produced a 38% increase over controls.

Example 2

Fetal Globin Production in Erythroid Cell Cultures.

Fetal globin production was determined in erythroid progenitor cells cultured in the presence or absence of test compositions. Erythroid cells were purified from blood obtained from a normal individual . (It is more difficult to induce fetal globin in the marrow and cell cultures of normal individuals than in that of patients' cultures). Erythroid cell cultures were established with the following conditions: IMDM methylcellulose media, erythropoietin (3 U/ml), the human subjects' mononuclear cells, 30% charcoal-adsorbed fetal calf serum, and the test compounds at varying micromolar concentrations. Positive control cultures were established using fetal calf serum alone, as fetal calf serum is a potent inducer of fetal globin expression. Charcoal-absorbed fetal calf serum was also used alone as a negative control, as it does NOT induce fetal globin expression.

Compounds were tested for their ability to induce expression of fetal globin expression in erythroid cell cultures established from the peripheral blood of normal individuals. Colonies were harvested and assayed for globin mRNA following 14 days of culture. Each compound was tested in 5 duplicate cultures from 2–4 individual human subjects. Globin expression was quantitated by RNase protection assay for % gamma globin as a fraction of total non-alpha globin (% gamma/gamma+beta globin mRNA).

Figure 11:
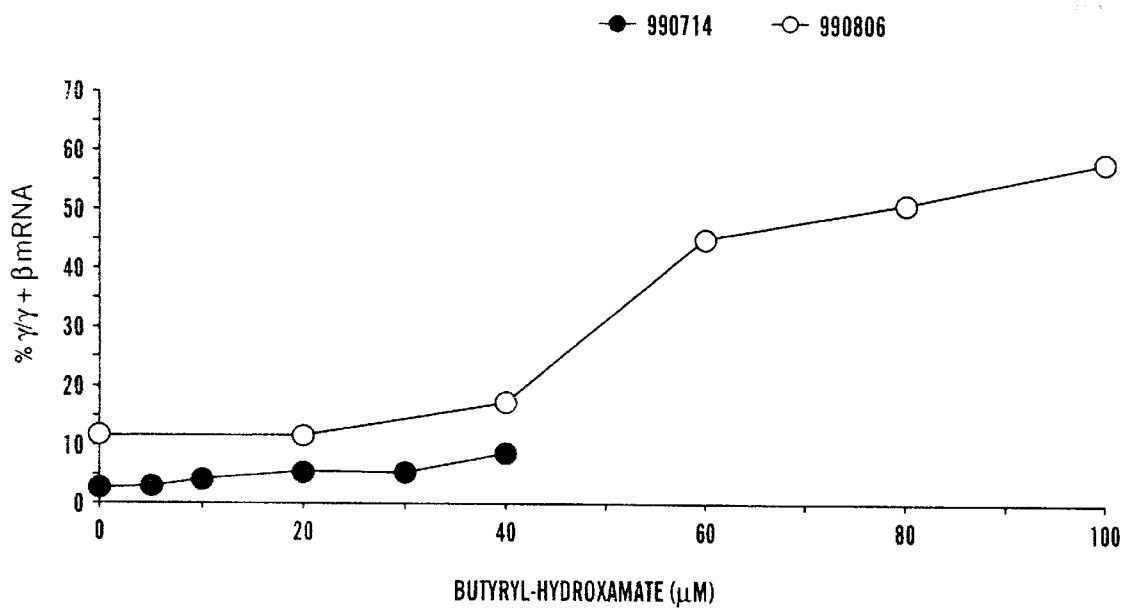
FIG. 11. Percentage $\gamma$-globin expression in erythroid cultures treated with butyryl hydroxamate.
Figure 11:
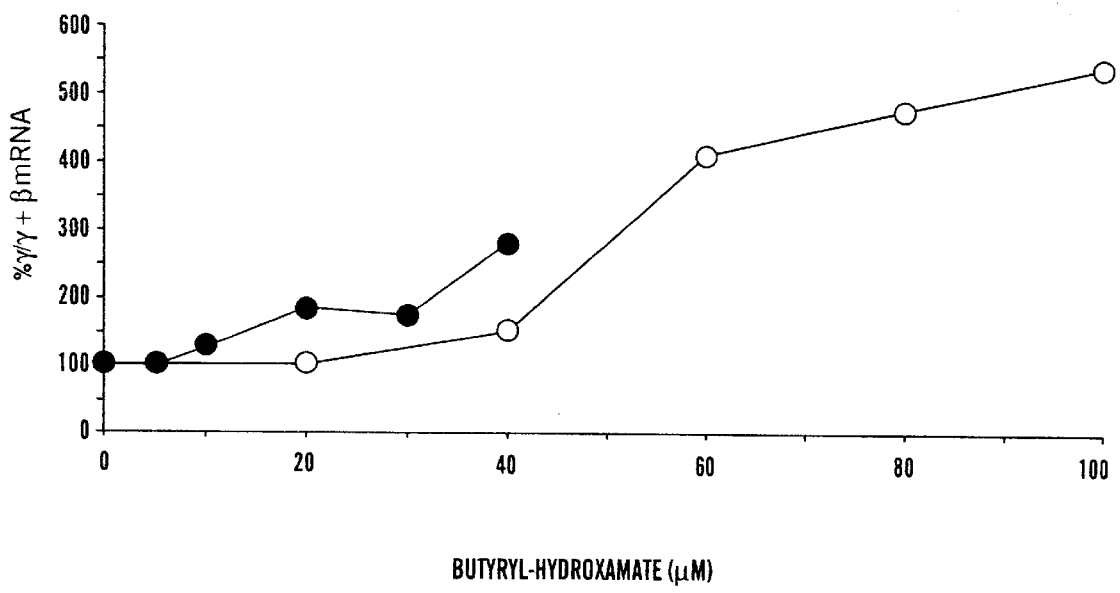

Three selected compounds were tested. Propionyl hydroxamate induced fetal (gamma) globin expression from 1.5–6.7-fold over control cultures at a concentration range of 5 to 150 micromolar (Table I). Suberoyl bis hydroxamic acid induced an increase in gamma globin expression by 1.5 to 10.8-fold over control cells at 1 to 12 micromolar concentrations (Table II). Butyryl hydroxamate induced gamma globin expression by 1.9- to 5.3-fold over control at concentrations from 10 to 100 micromolar (Table III and FIG. 11).

Each of these compounds induced more gamma globin than the positive control, fetal calf serum. This degree of induction of gamma globin and the low concentrations required demonstrates potent fetal globin inducing activity, at concentrations that are approximately a log lower than previously reported inducers of fetal globin expression. The specific results for each experiment are shown in Tables I, II, and III, and FIG. 11.

TABLE I

PERCENTAGE γ-GLOBIN EXPRESSION IN ERYTHROID CULTURES TREATED WITH PROPIONYL HYDROXAMATE

|  | γ/γ + β | | mean | x increase |
|---|---|---|---|---|
| 990709 | 99-4 | 99-5 | | |
| FCS | 5.18 | 7.61 | 6.40 | |
| ChFCS | 1.12 | 2.23 | 1.68 | 1.0 |
| 1 μM | 1.39 | 2.39 | 1.89 | 1.1 |
| 8 μM | 1.19 | 1.73 | 1.46 | 0.9 |
| 10 μM | 1.86 | 3.28 | 2.57 | 1.5 |
| 50 μM | 3.80 | 6.40 | 5.10 | 3.0 |
| 100 μM | 7.78 | 8.80 | 7.72 | 4.6 |
| 991208 | 00-1 | 00-3 | | |
| FCS | 16.09 | 23.02 | 19.56 | |
| ChFCS | 8.29 | 8.23 | 8.26 | 1.0 |
| 25 μM | 12.17 | 12.38 | 12.27 | 1.5 |
| 50 μM | 20.79 | 21.30 | 21.05 | 2.5 |
| 100 μM | 32.74 | 38.33 | 35.54 | 4.3 |
| 125 μM | 37.83 | 39.14 | 38.49 | 4.7 |
| 150 μM | 59.60 | 51.56 | 55.58 | 6.7 |
| 0601-0 | 00-3 | | | |
| FCS | 8.05 | | 8.05 | |
| ChFCS | 3.89 | | 3.89 | 1.0 |
| 50 μM | 9.57 | | 9.57 | 2.5 |
| 100 μM | 16.66 | | 16.66 | 4.8 |
| 150 μM | 24.40 | | 24.40 | 6.3 |

TABLE II

PERCENTAGE γ-GLOBIN EXPRESSION IN ERYTHROID CULTURES TREATED WITH SUBEROYL BIS HYDROXAMIC ACID

|  | γ/γ + β | | | mean | x increase in % s |
|---|---|---|---|---|---|
|  | 99-3a | 99-3b | | | |
| FCS | 25.89 | 24.86 | | 26.38 | |
| ChFCS | 7.70 | | | 7.70 | 1.0 |
| 0.5 μM | 13.54 | 11.55 | | 12.55 | 1.6 |
| 1 μM | 10.99 | 9.19 | | 10.09 | 1.3 |
| 2 μM | 21.36 | 23.63 | | 22.50 | 2.9 |
| 3 μM | 24.90 | 23.72 | | 24.31 | 3.2 |
| 4 μM | 48.57 | 50.66 | | 49.62 | 6.4 |
|  | 99-4 | 99-5 | | | |
| FCS | 14.48 | | | 14.48 | |
| ChFCS | 7.19 | 6.79 | | 6.99 | 1.0 |
| 0.5 μM | 6.25 | 6.42 | | 6.34 | 0.9 |
| 1 μM | 8.46 | | | 8.46 | 1.2 |
| 2 μM | 9.92 | 10.65 | | 10.29 | 1.5 |
| 3 μM | 17.99 | 17.89 | | 17.94 | 2.6 |
| 4 μM | 24.10 | | | 24.10 | 3.4 |
|  | 99-6 | 99-7 | 99-10 | | |
| FCS | 12.03 | 23.93 | 16.36 | 17.44 | |
| ChFCS | 3.04 | 6.79 | 5.36 | 5.06 | 1.0 |
| 1 μM | 5.41 | 10.76 | 6.92 | 7.70 | 1.5 |
| 2 μM | 6.65 | 15.75 | 10.00 | 10.80 | 2.1 |
| 4 μM | 13.33 | 30.45 | 15.73 | 19.84 | 3.9 |
| 6 μM | 22.97 | 31.51 | 29.15 | 27.88 | 5.5 |
| 8 μM | 31.99 | 44.02 | 35.73 | 37.25 | 7.4 |
|  | 99-10 | 00-1 | 00-3 | | |
| FCS | 13.17 | 5.85 | 6.57 | 8.46 | |
| ChFCS | 6.18 | 2.38 | | 4.28 | 1.0 |
| 4 μM | 11.38 | 4.82 | 5.01 | 7.07 | 1.7 |
| 6 μM | 16.34 | 9.46 | 8.89 | 11.56 | 2.7 |
| 8 μM | 21.37 | 12.88 | 21.68 | 18.64 | 4.4 |
| 10 μM | 35.06 | 27.89 | 31.25 | 31.40 | 7.3 |
| 12 μM | 46.94 | | 45.69 | 46.32 | 10.8 |

TABLE III

PERCENTAGE γ-GLOBIN EXPRESSION IN ERYTHROID CULTURES TREATED WITH BUTYRYL HYDROXAMATE

|  | γ/γ + β | | mean | x increase |
|---|---|---|---|---|
|  | 99-4 | 99-5 | | |
| FCS | 8.87 | 9.72 | 9.30 | |
| ChFCS | 2.95 | 2.65 | 2.80 | 1.0 |
| 6 μM | 2.29 | 3.40 | 2.85 | 1.0 |
| 10 μM | 3.44 | 4.06 | 3.75 | 1.3 |
| 20 μM | 4.43 | 6.06 | 6.25 | 1.9 |
| 30 μM | 4.12 | 5.35 | 4.74 | 1.7 |
| 40 μM | | 7.72 | 7.72 | 2.8 |
|  | 99-6 | 99-7 | | |
| FCS | 17.20 | 22.17 | 19.69 | |
| ChFCS | 7.00 | 14.57 | 10.79 | 1.0 |
| 20 μM | 8.65 | 12.49 | 10.57 | 1.0 |
| 40 μM | 14.81 | 17.39 | 16.10 | 1.5 |
| 60 μM | 37.65 | 51.04 | 44.35 | 4.1 |
| 80 μM | 44.98 | 55.39 | 50.19 | 4.7 |
| 100 μM | 54.06 | 60.90 | 57.48 | 5.3 |

Example 3

Erythroid Proliferation in the Presence of GM-CSF, SCF and EPO.

Figure 2A:
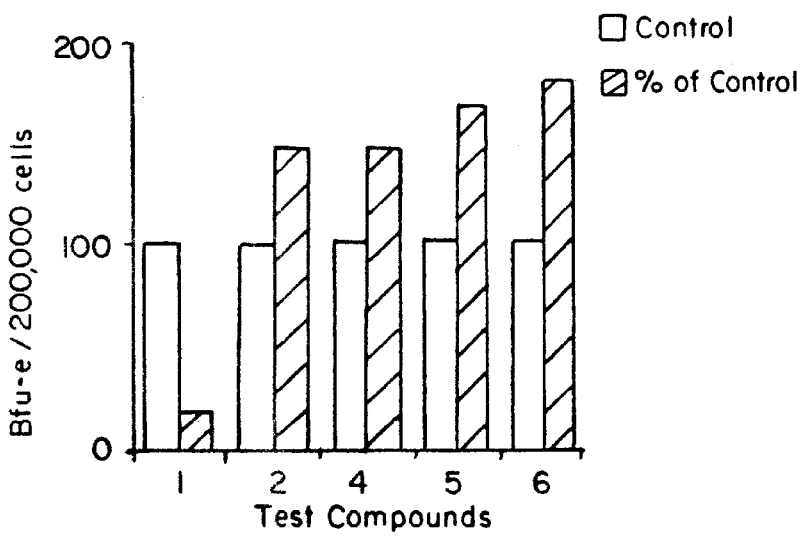
FIG. 2. Effects of tested compounds on erythroid colony (Bfu-e) proliferation in cultures from (A) a normal individual, (B) a sickle cell patient, and (C) fetal liver stem cells.

Erythroid cells were obtained, as described in Example 1, from a normal subject and cultured on semi-solid medium in the presence of a maximal amount of erythroid growth factors including IL-6, GM-CSF, SCF and EPO. Erythroid proliferation in the presence of these factors is expected to be maximal and, therefore, any increases observed would be significant. As shown in FIG. 2A, colonies were grown in the presence or absence of: lane 1, 0.1 mM arginine butyrate (16% of control); lane 2, 0.5 mM 2-(4'-methoxyphenoxy) propionic acid; lane 3, α-methylhydrocinnamic acid; lane 4, 0.2 mM phenoxyacetic acid; and lane 5, 0.2mM 4-chlorophenoxy-2-propionic acid. As shown, all of these test compositions were able to further increase Bfu-e growth.

Figure 2B:
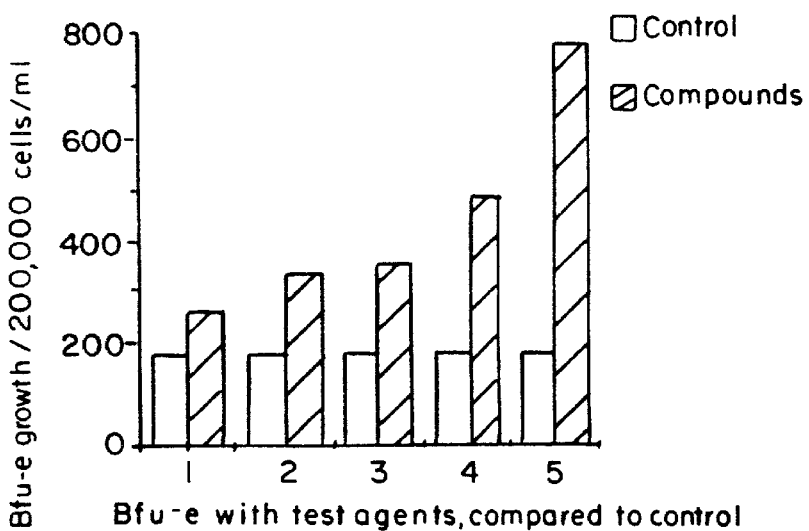

In a second experiment, erythroid progenitor cultures were established from a patient with sickle cell anemia and plated with maximal growth factors and the compositions. As shown in FIG. 2B, responses to this set of compositions were similar to the effects observed with normal human Bfu-e: Lane 1, α-methylhydrocinnamic acid; Lane 2, 2-(4'-methoxyphenoxy)propionic acid; Lane 3, 2,2-dimethylbutyric acid; Lane 4, phenoxyacetic acid; and Lane 5 phenoxyacetic acid. Agents were tested at between 0.1 mM and 0.2 mM. Thus, effects could not be attributable solely to the influence of the erythroid growth factors added.

Figure 2C:
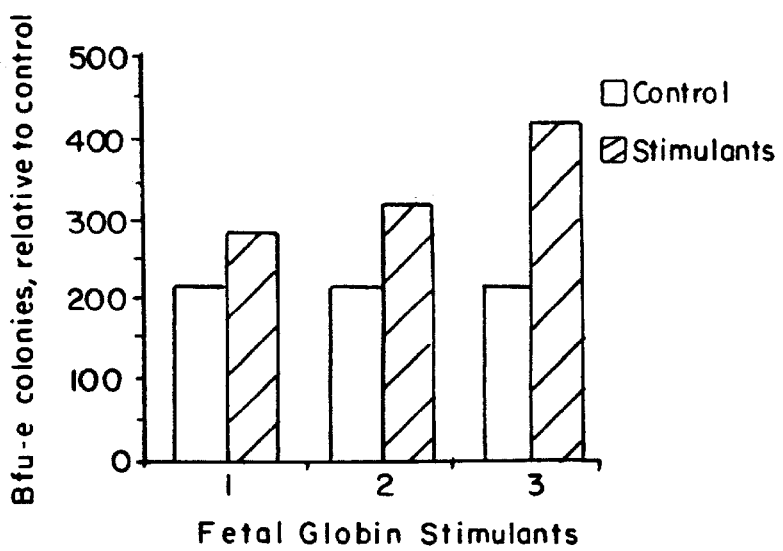

In a third experiment, human fetal liver cells were also tested. As fetal cells are known not to respond to the presence of the growth factors, any increases observed are highly significant. Erythroid progenitor cultures were established from fetal liver and plated with maximal amounts of growth factors. To these plates were added; lane 1, 2-(4'-methoxyphenoxy) propionic acid; lane 2, phenoxyacetic acid; and lane 3, α-methylhydrocinnamic acid; all at a concentration of 0.2 mM. As shown in FIG. 2C, all plates showed increased proliferation of colonies and increases were determined to be significant (p<0.025).

In a fourth experiment, erythroid cells were obtained from a sickle cell patient. These cells were established in culture both with and without test a variety of test compounds. Cultures were incubated for 14 days in methylcellulose media with maximal concentrations of all hematopoietic growth factors (GM-CSF, SCF, EPO). Colonies were analyzed using fluorescent monoclonal antibodies against fetal globin to determine the proportion of erythroid cells that expressed fetal globin. These results are shown in Table IV.

TABLE IV

PROPORTION OF FETAL GLOBIN-EXPRESSING CELLS IN CULTURE

| Test Agent | Increase in γ-Globin Expressing Cells |
|---|---|
| Controls (growth factors only) | 40.7% |
| Phenoxyacetic Acid (0.2 mM) | 54.6% |
| 4-chloro-2-phenoxypropionic acid (0.5 mM) | 59.7% |
| Fumaric Acid Monoethyl Ester | 59.1% |
| Alpha-methylhydrocinnamic Acid | 64.4% |
| 2,2-dimethylbutyric Acid | 70.1% |

As shown, increases in fetal globin expressing cells were detected from 13.9% to 29.4% above control colonies from the same subject.

Example 4
Pulse Administration of Phenoxyacetic Acids and Phenylakylacids.

Figure 3A:
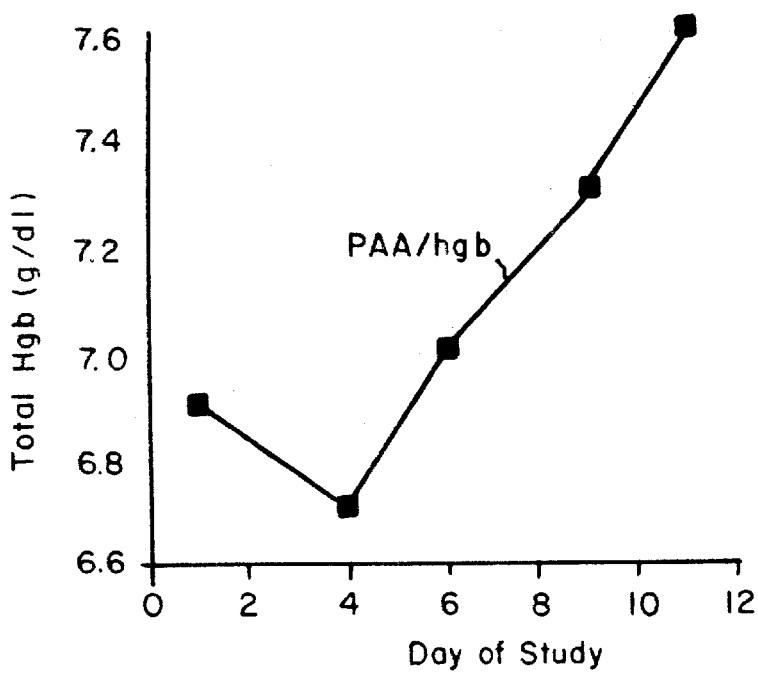
FIG. 3. Comparison of (A) pulse treatment of a baboon with phenoxyacetic acid verses (B) continuous treatment with EPO.
Figure 3B:
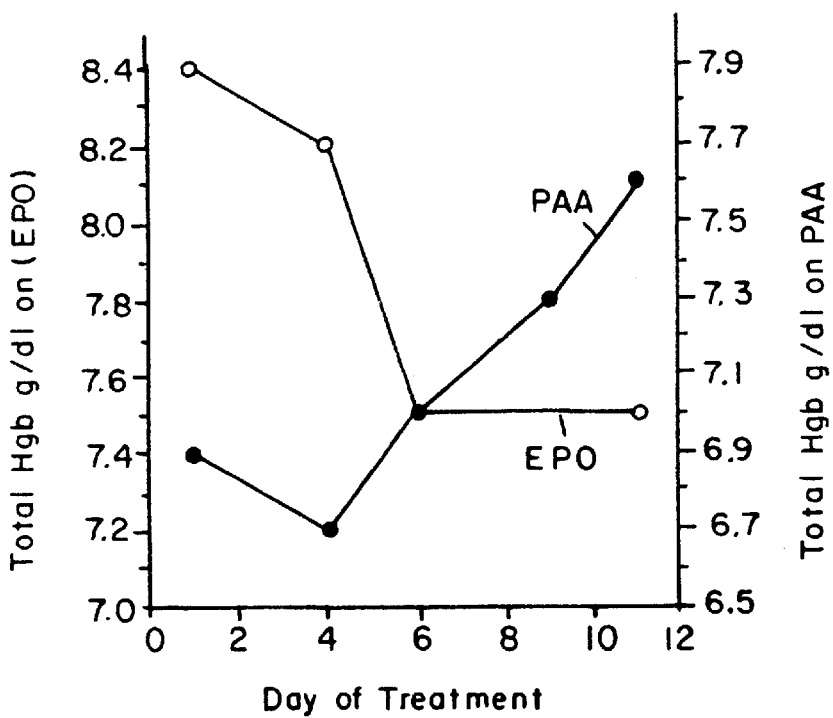

As discussed, compositions were more effective given as pulse therapy than as continuous therapy in baboons. Therapy was administered to anemic baboons who were being phlebotomized 5–10 ml/kg of blood per day on a continuous basis. EPO was administered daily at 300 U/kg/dose. Arginine butyrate was administered daily at 700 mg/kg/day for 5 days and phenoxyacetic acid at 500 mg/kg/day daily over 8 hours and at 1000 mg/kg/day for 24 hours/day daily for five days each. Total hemoglobin on these four continuous treatment schedules did not increase in the presence of anemia due to phlebotomy. As shown in FIG. 3B, with continuous treatment with EPO, hemoglobin declined from 8.2 to 6.9 gm/dl. This same baboon showed no rise when treated with EPO at 300 units/kg 3 times per week. With continuous arginine butyrate treatment, hemoglobin remained essentially stable at 6.7 to 6.9 gram/dl. With continuous treatment with phenoxyacetic acid, hemoglobin levels remained stable at 7.0 gram/dl to 6.9 gram/dl during 8 hour therapy and declined from 6.8 to 4.5 when the drug was given for 24 hours per day for 5 days.

In contrast, administration of pulse doses of phenoxyacetic acid (2 oral doses per week, given as 500 mg/kg on days 1 and 4, resulted in rises in total hemoglobin from 6.9 to 7.6 gram/dl in one week (FIG. 3A), a time frame which is consistent with the development of red blood cell precursors in the baboon. These results show that pulse therapy of phenoxyacetic acid (PAA) is superior to continuous delivery of this same compound. In a similar experiment, platelet counts increased from 240,000 to 767,000 with pulse administration of dihydrocinnamic acid. Treatment courses demonstrate that "less is more" or pulse therapy is surprisingly effective in an animal model very close to humans. Furthermore, the pulsed method of administering PAA was more effective than was administration of EPO at 300 U/Kg/dose, which is considered therapeutic at this dose for many forms of anemia.

Example 5
Amino Acid Uptake of Erythroblasts in the Presence of Compositions.

Figure 4:
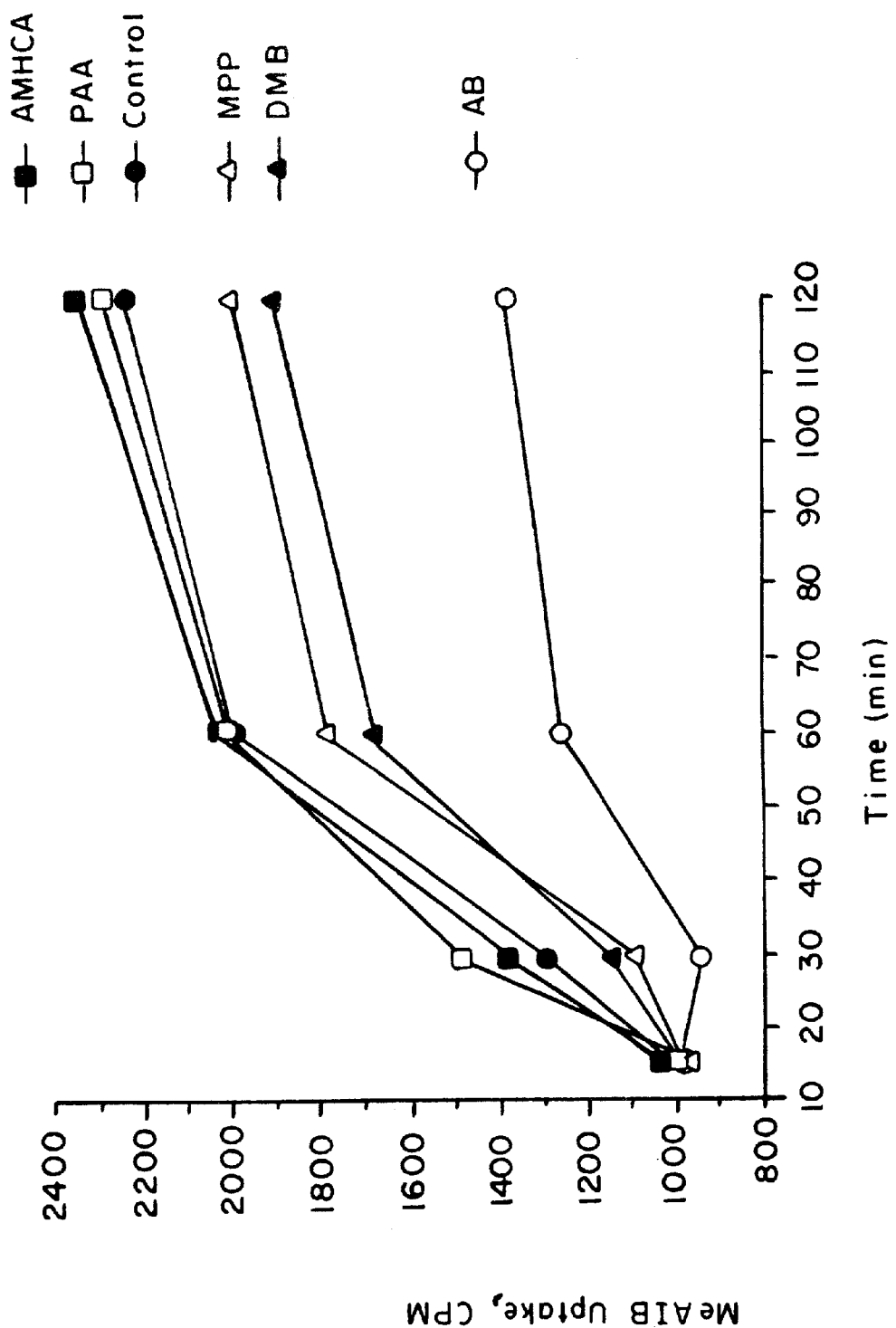
FIG. 4. Uptake of radio-labeled neutral amino acid ($^3$H-methyl-aminoisobutyric acid) into erythroblasts incubated in the presence of various test compounds.

Erythroblasts were tested for alterations in uptake of radio-labelled amino acid ($^3$H-methyl-aminoisobutyric acid; MeAIB) in the presence of AB (arginine butyrate), AMHCA (α-methylhydrocinnamic acid), PAA (phenoxyacetic acid), and IBT (isobutyramide), each at 2.0 mM. As shown in FIG. 4, treatment produced a marked reduction in the transport of this synthetic amino acid, compared to uptake into untreated (control) fetal liver erythroid cells. Arginine butyrate inhibited amino acid uptake relative to untreated (control) cells or cells incubated with phenoxyacetic acid, fumaric acid monoethyl ester, diethyl butyric acid or α-methylhydrocinnamic acid, which did not inhibit amino acid transport. 2-(4'-methoxyphenoxy) propionic acid (MPP) and 2,2-dimethylbutyric acid (DMB) treatment produced a moderate inhibition of transport. Even after 30 minutes, most compounds exhibited a marked decrease in MeAIB uptake. After 60 and 120 minutes, inhibition was most significant with arginine butyrate and somewhat less so with MPP and DMB. These results indicate that these compounds have at least some effect on amino acid uptake and, possibly, cell viability.

Example 6
Hematological Efficacy of Pulse Therapy.

Increased expression of fetal hemoglobin (Hb F) to adequate levels can ameliorate sickle cell disease. While any increase in Hb F can have ameliorating effects, and 8.5% Hb F prevents early mortality, 20% Hb F or more is generally considered necessary to ameliorate clinical symptomatology. This 20% Hb F level was achieved in 8% of subjects receiving hydroxyurea treatment on a national study, but remains a therapeutic goal for the majority of patients.

To determine if arginine butyrate can be used for therapeutic benefit, two low-dose regimens of butyrate were studied. Treatment were given intermittently either weekly, or in a pulse fashion, at 2–3 week intervals. Twenty-two treatment courses were examined with 300+ weeks of patient observation, including 18 months of home therapy.

Weekly therapy produced biochemical (Hb F) responses in 8/10 patients and increases in total Hb by 1–4 gram/dl above baseline levels, in 6/10. However, Hb F responses were in the 4–10% range, and total Hb levels declined to half the initial rise with continued weekly therapy.

In contrast, pulse therapy produced the desired hematologic responses in 8 of 12 sickle cell and beta thalassemia patients. Hb F levels increased 3-to 5-fold above baseline to greater than 20% in 4/6 adult sickle cell patients. A S5-year old patient reached 29% Hb F, and severe symptoms abated. The baseline Hb F level in responders was 2–6%. Total Hb levels increased by 2–3 grams/dl to >9.0 gm/dl in 4/6 severe thalassemia patients. The pulse regimen eliminated previous transfusion-dependency in thalassemia major and reduced iron stores, perhaps from mobilization of available stored iron into healthy red blood cells.

These results demonstrate that butyrates can be titrated to produce desired therapeutic goals for amelioration of beta globin disorders, and the fetal globin genes can be induced to high level expression at any age, from baseline levels of 2% or more.

Example 7

Long Term Pulse Therapy.

Patients were treated by pulse therapy for 4–18 months with arginine butyrate. Patient's fetal globin genes were found to be reactivated to a degree that significantly compensated hematologically for defective adult β globin genes in greater than fifty percent of patients (8 out of 12). It is preferred to avoid prolonged treatment with high doses of butyrate, which cause cellular growth arrest in G1, and can enhance the accelerated apoptosis of beta thalassemia. Partial tolerance observed with long-term weekly therapy appears related to erythroid cell growth arrest and a decline in EPO levels as Hgb and Hct rise and depletion of available iron stores. Treatment with additional doses of iron supplements can overcome some of the anti-proliferative activities of butyrate in vitro. Time required on therapy has been only 25%–35% of the treatment days per month necessary for effective transfusion and iron chelation. This has improved the quality of life of some patients.

Example 8

Comparison of Conventional verses Pulse Treatment.

Figure 5A:
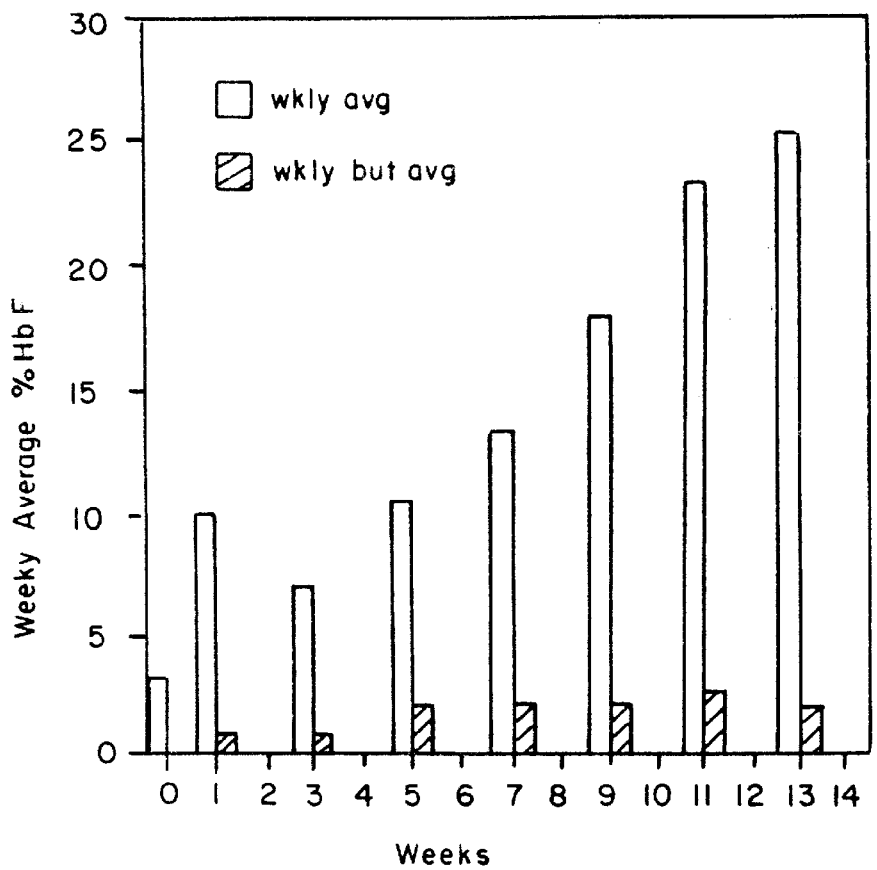
FIG. 5. Comparison of (A) conventional verses (B) pulse treatments.

Conventional treatment: A 44-year old patient with sickle cell disease was tested with arginine butyrate at 750 mg/kg. Drug was administered by infusion for 10–16 hours per day and 5 days/week. As shown in FIG. 5A, percent total HbF increased from 3% to about 15–18%. After 150 days, total HbF declined to about 10%.

Figure 5B:
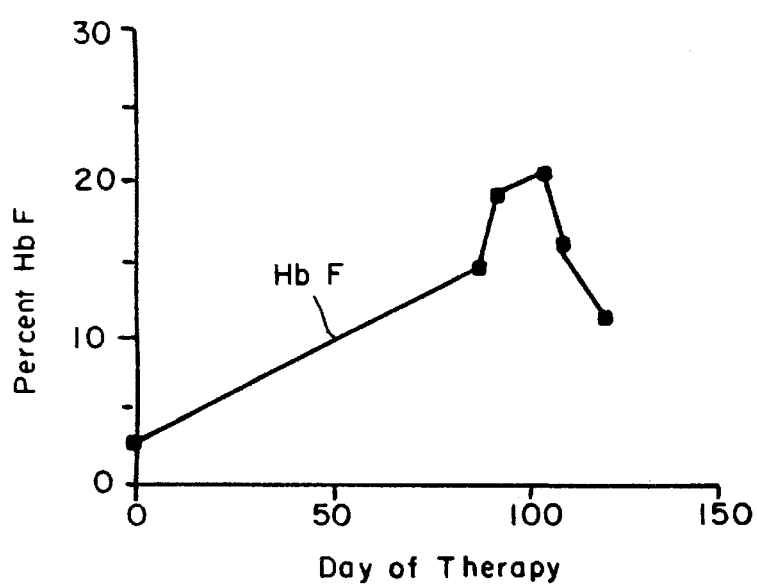

Pulse treatment: Treatment of the same sickle cell patient as above was changed from weekly to pulse administration of arginine butyrate about one year later (FIG. 5B). Arginine butyrate was administered by infusion at 500 to 750 mg/kg for 4 days for about 10–16 hours per day. After the 4 day regimen, drug was withheld for 10 days before treatment was repeated. This regimen was continued for about 5 months and percent total fetal hemoglobin increased to over 20%. This level was maintained until treatment was discontinued. Hemoglobin F levels above 20% are generally considered to be sufficient to eliminate symptoms associated with sickle cell disease.

Example 9

Stimulation of Fetal Globin Production without Cellular Growth Arrest.

As demonstrated in Example 5, stimulation of fetal globin production can ameliorate β-globin disorders, however butyrate can also induce cellular growth arrest. To determine if these potentially opposing actions can be balanced for therapeutic effect, two intermittent schedules of butyrate were compared in 21 treatment courses in 14 patients ages 3 to 55 years, with sickle cell disease or β thalassemia. An optimal dose was identified on an individual patient regimen and continued on a weekly basis in eleven patients. Providing 7 to 14 days without any drug exposure to facilitate proliferation of treated cells, an alternate week regimen or pulse therapy, was administered to twelve patients (see Tables V, VI and VI).

A series of ten patients with sickle cell anemia and β-thalassemia were treated with continuous therapy with arginine butyrate. In 3 out of 4, transfusion requirement was diminished. Four patients had a decline or plateau following this initial rise in total hemoglobin. The mean peak in total HgB which was detectable in the ten patients over their baseline was 1.6 gm/dl.

TABLE V

WEEKLY THERAPY

| Age (yrs) | sex | Condition | weeks | F-retics Base | On | Increase in Total Hgb | Comments |
|---|---|---|---|---|---|---|---|
| 34 | F | βIVS II-745 | 7 | 4 | 16 | 3 | six weeks of therapy |
| 3 | M | β(-39-39) | 8 | 60 | 77 | ND | AIHA, trans. cont. |
| 4 | M | βIVS I, 1-6 | 40 | 56 | 75 | +4.3 | response declined |
| 40 | M | frameshift 5 | 5 | 0.5 | 1 | +1.0 | response declined |
| 42 | F | Hb SS | 24 | 12.7 | 35.3 | +2.0 | response declined |
| 25 | M | β-39,-39 | 8 | 76 | 68 | 1.5 | plateaued |
| 7 | F | β-39-87 | 16 | 64.7 | 67.3 | +2.3 | changed to pulse |
| 21 | F | HbS, β-39 | 6 | 4 | 20 | ND | transfusions cont. |
| 3 | F | HbE/? | 9 | 42 | 52.7 | ND | transfusions cont. |
| 31 | F | HbSS | 4 | 14 | 30.7 | +1.0 | response declined |

As shown in Table V, increases in total Hb occurred in some patients. However, in most cases hemoglobin levels declined to half of the initial increase above baseline when therapy was continued daily and weekly.

Patients were next administered a pulse therapy regimen. Each session comprised eight to twelve hours of nightly infusions. Patients received treatments for two to three nights followed by 7 to 21 days without any therapy. Total increases in Hgb were sustained as high as 3.0 g/dl above baseline levels with a mean increase of 2.1 g/dl in 8 out of 12 patients (p<0.05, paired t-test, chi square). Importantly, these responses did not decline over time.

TABLE VI

PULSE THERAPY

| Age (yrs) | Sex | Condition | weeks | F-cells Base | On | F-retics Base | On | Percent HbF Base | HbF On | Increase Total Hgb |
|---|---|---|---|---|---|---|---|---|---|---|
| 44 | F | HbSS | 11 | 28 | 58 | 18 | 25 | 3 | 24 | +1.0 |
| 55 | F | HbSS | 28 | 42 | 56 | 18 | 36 | 6 | 29 | +1.0 |
| 30 | F | HbSS | 18 | 50 | 65 | 35 | 46 | 8 | 35 | +2.0 |
| 29 | M | HbSS | 15 | 23 | 59 | 12.6 | 24 | 6.9 | 22 | +2.0 |
| 34 | F | HbSS | 7 | 11 | 8 | 8 | 9.3 | 0.5 | 1.5 | ND |
| 18 | F | HbSS | 9 | 15 | 0.5 | 0.7 | 6.7 | 0.5 | 1.0 | ND |

TABLE VII

PULSE THERAPY

| Age (yrs) | Sex | Condition | Weeks | F-cells Base | On | Non-∀/∀* Base | On | Increase in Total Hgb |
|---|---|---|---|---|---|---|---|---|
| 25 | M | β-39 | 7 | 100 | 100 | 0.4 | 0.9 | 3.0 |
| 7 | F | β-39-87 | 68 | 29 | 100 | 0.6 | 1.1 | 3.6 |
| 27 | M | βIVS I-1 | 4 | 100 | 100 | 0.5 | 0.9 | 2.1 |
| 26 | M | HbE/? | 15 | 79 | 84 | 0.17 | 0.25 | 1.7 |
| 43 | M | frameshift-5 | 24 | 100 | 100 | 0.5 | 0.75 | |
| 17 | F | βIVS II | 33 | 10 | 16 | 0.5 | 0.7 | ND |

*= non-α: α globin chain synthesis ratios

As shown in Tables VI and VII, pulse therapy results were significantly improved compared to weekly therapy. Percent HbF levels increased to above 20% for 4 of 6 patients treated and non-α/α globin chain ratios were at or near 1.0. These results are sufficient to overcome symptoms in the responsive sickle cell patients as well as in the same proportion of thalassemia patients (about 2/3).

Pulse regimens differ from other reported sickle cell therapy regimens in requiring smaller doses and less onerous delivery methods. Delivery in regimen one and regimen two is limited to 4 to 7 grams of butyrate per kilogram body weight per month while other therapy regimens require the delivery of 40 to 48 grams per kilogram body weight per month. Thus, the total amount of drug delivered is only ten to fifteen percent of the doses used in other treatment methods.

Benefits of the pulse treatment include reduced dose and reduced treatment time. Pulse treatments only require the delivery of 4 to 7 grams per kilogram body weight per month compared to 40 to 48 grams per kilogram body weight per month. Furthermore, pulse treatments only require 6 to 10 hour nightly infusions for a total of six to nine days per month while other methods require 24 hour infusions for 20–24 days per month. Surprisingly, pulse therapies avoid erythroid cell growth arrest, which is a problem with conventional therapies.

Weekly therapy produced biochemical increases in fetal globin expression in 8/11 patients and rises in total hemoglobin by a mean of 1.6 gm/dl in and 2.4 gm/dl in the 6 responsive patient (6/9 treated). However, hematologic effects frequently declined to half the initial rise when weekly treatment was continued Pulse therapy resulted in a 2- to 5-fold increase above baseline HbF levels to the desired 20% Hb F threshold, or higher, in 4/6 sickle cell patients and produced a further rise in total hemoglobin above baseline in 4/6 beta thalassemia patients. Transfusion-dependency was eliminated and iron stores were depleted in two patients with previously transfusion-dependent thalassemia major. No significant adverse side effects were observed with up to 17 months of home therapy and 350 weeks of patient treatment.

These results demonstrate that pulse administration of relatively low doses of a natural fatty acid can stimulate γ globin production to a therapeutic degree in two-thirds of patients with beta globin gene disorders.

Continuous 24 hour per day infusions of was administered in another study to 10 patients with sickle cell disease and beta thalassemia and produced rises in fetal globin in a lower proportion of patients, 40%. Many of these responses were not sustained.

Therefore, the same infusion rate given for 24 hours/day results in a lower response rate than does 8–16 hour/day treatment at the same infusion rate. A lower proportions of patients respond hematologically with continuous 24 hours therapy (1/10 patients) than respond to intermittent pulse therapy 8/10 patients. Hematologic responses are higher with pulse therapy (2–5) gram/dl above baseline levels compared to no responses in patients treated with 24 hour therapy.

Example 10

Pulse Therapy Produces a Sustained Response.

Figure 6A:
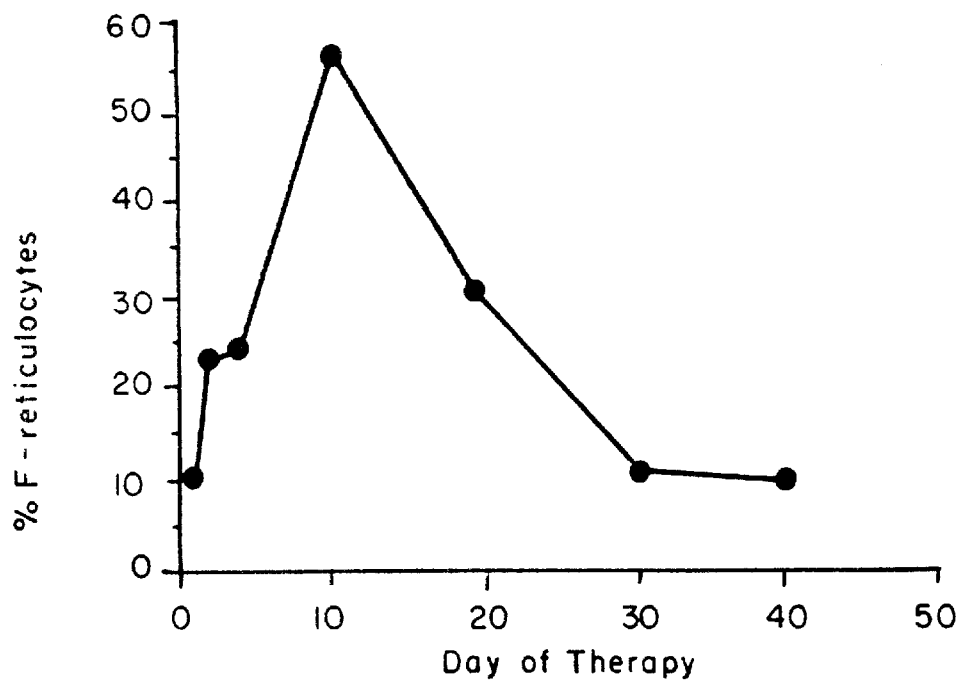
FIG. 6. Sustained response observed comparing (A) continuous verses (B) pulse therapy.
Figure 6B:
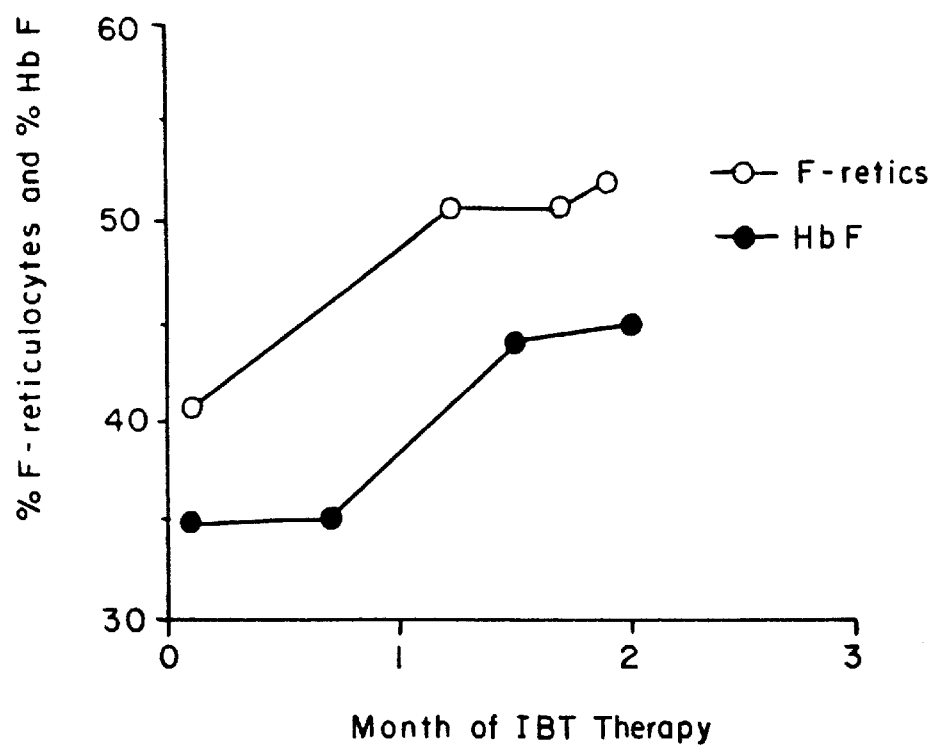

A comparison of continuous daily therapy and intermittent pulse therapy of with isobutyramide oral solution demonstrated that continuous daily therapy results in drug tolerance or a loss of drug effect. This is illustrated in an adult and in a child with sickle cell anemia who were receiving continuous daily isobutyramide oral solution at escalating doses from 25 to 300 mg/kg/day. The response of induction of fetal hemoglobin producing reticulocytes, or new red blood cells, rose and then declined back to baseline on continued therapy (FIG. 6A). In contrast, in a 25 year old male patient with beta thalassemia treated with pulse therapy of isobutyramide oral solution (at 40 mg/kg dose) as 3 pulses per week, the F-reticulocytes increased progressively and did not decline (FIG. 6B).

Example 11
Effects of Continuous Therapy.

Figure 7:
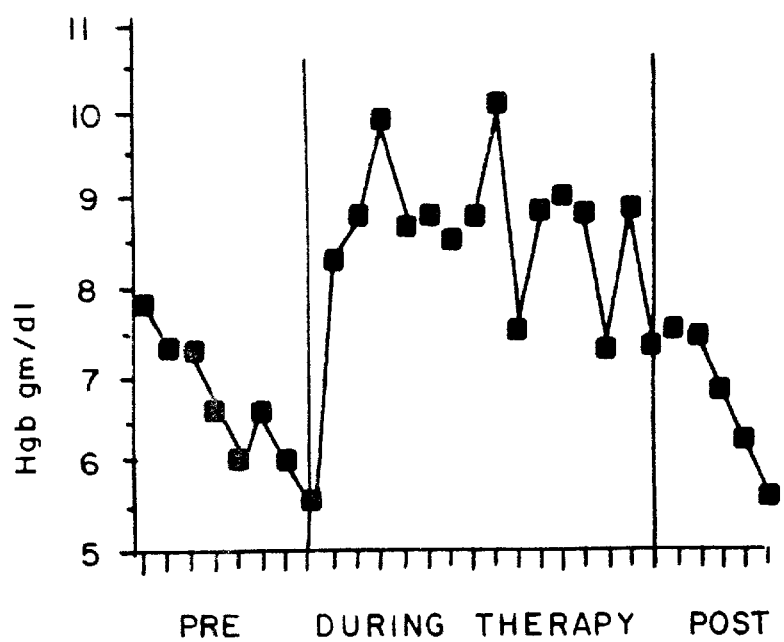
FIG. 7. Total hemoglobin levels in a patient on continuous therapy.

An example of the effects of continuous therapy is shown in a 4-year old child with beta thalassemia treated for 10 months with continuous therapy (FIG. 7). Treatment period, the ten month duration of butyrate therapy, is shown between the vertical lines. A rise from a total hemoglobin from a baseline of 5.6 grams/dl to a peak of 9.9 gm/dl occurred, then plateaued at 8.0–8.8 gm/dl for 2 months. After 4 months of continuous weekly treatment, total hemoglobin levels declined to 7.5–8.4 gm/dl, suggesting a growth arrest affect or drug tolerance. When treatment was discontinued, total hemoglobin declined back to the patient's baseline of 5.6 gm/dl.

Example 12
Examples of Pulse Therapy.

Figure 8:
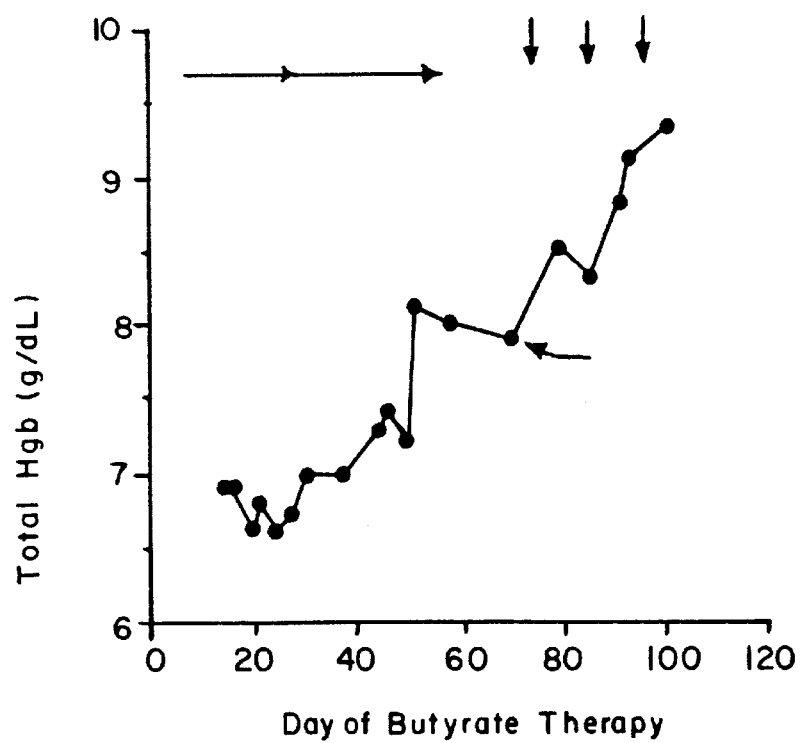
FIG. 8. Total hemoglobin levels in a patient switched from continuous to pulse therapy.

A plateau or even a decline in hematologic response has been commonly observed when butyrate therapy is given continuously. This is illustrated in a patient with $\beta°$ thalassemia, who responded to weekly butyrate treatment with an increase in fetal globin synthesis and improved globin chain balance from 0.5 to 0.85 non-$\alpha$ to $\alpha$-globin chain ratios (FIG. 8). A 3-fold increase in $\gamma$ globin mRNA was detected 24–36 hours after therapy. A 1–1.5 gram/dl rise in total hemoglobin followed the increase in $\delta$ globin synthesis and mRNA, but total Hgb then plateaued and even declined slightly (solid line). A decline in ferritin is also frequently observed (lower panel), even though the patient received single daily supplements.

When therapy was decreased to shorter pulses for 2–3 days on alternate weeks, total hemoglobin rose another 2 grams/dl. Increased iron supplements were required to support the active erythropoiesis, despite the presence of iron overload.

This figure illustrates the improved therapeutic effect between continuous therapy (to day 60) shown by the horizontal lines, and pulse therapy, shown by the vertical lines in a patient with beta thalassemia (FIG. 8).

The therapeutic rise in total hemoglobin plateaued or declined on weekly therapy. With a change to pulse therapy, shown by the curved arrow, there was a further rise in total Hgb to 9.6 gm/dl, a level that no longer requires transfusions.

Example 13
Reduced Infusion Rates Minimize Adverse Effects of Treatment.

Infusion rates were varied between 20 to 150 mg per kg per hour in several patients who have large proportions of circulating nucleated erythroblasts. Globin chain synthesis was assayed at different time points before and following drug infusions.

Figure 9A:
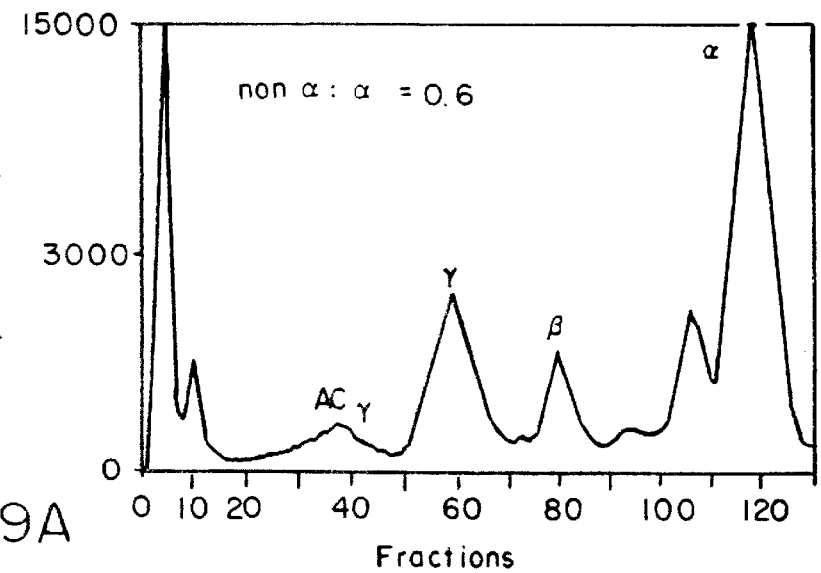
FIG. 9. $\alpha$, $\beta$ and $\gamma$ globin levels in a patient (A) before treatment, (B) at moderate dose treatment, and (C) at high dose treatment.
Figure 9B:
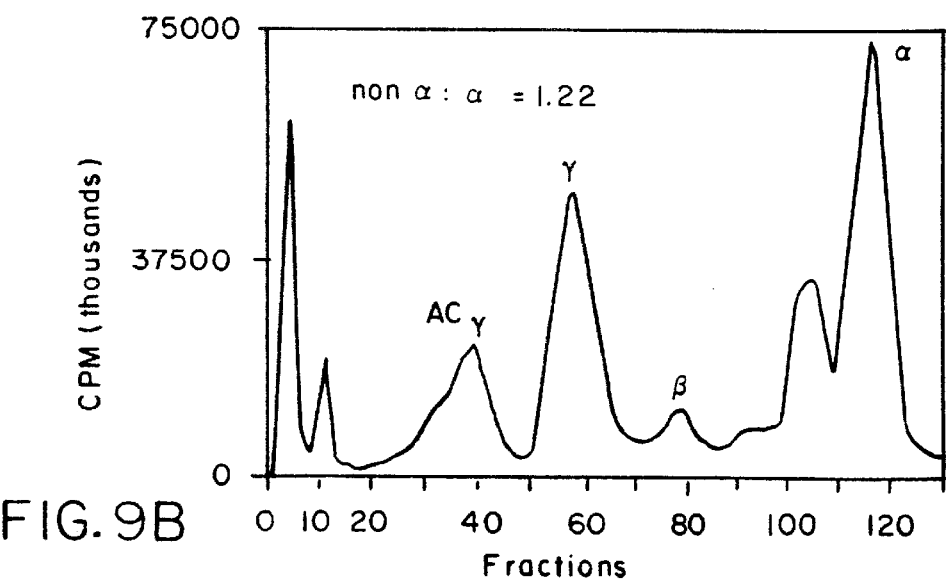

In a patient with $\beta+$ thalassemia, high doses of butyrate suppressed both $\gamma$ and $\beta$ globin chain synthesis (FIG. 9B), causing an overall globin balance worse than the original baseline (FIG. 9A). In contrast, lower infusion rates increased $\gamma$ globin synthesis and corrected globin chain ratios close to a normal range.

Figure 9C:
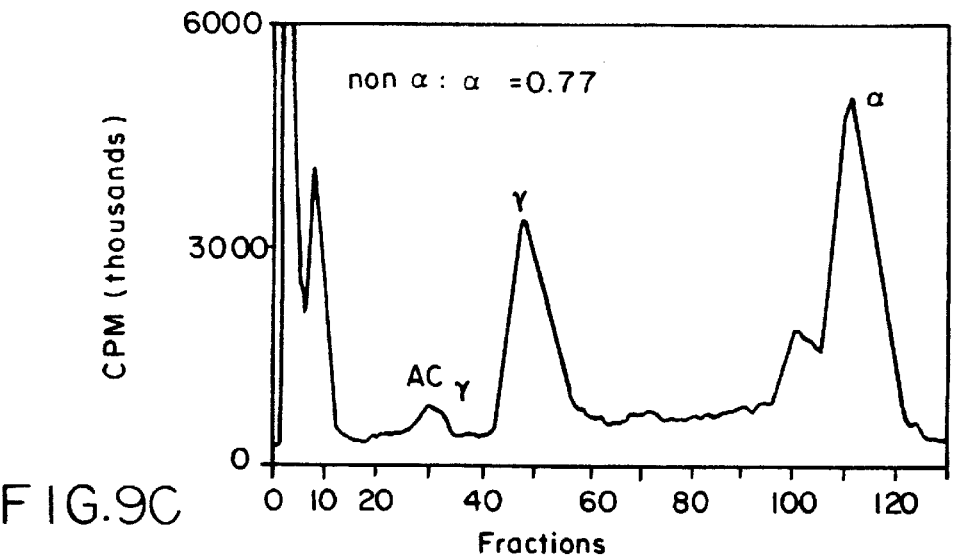

Similar results were observed in another patient. Infusion at 150 mg per kg per hour completely suppressed $\beta$ globin synthesis, although total globin chain balance was still improved (0.77 non-$\alpha$ globin to $\alpha$ globin ratio) over the patient's baseline level of 0.6 (FIG. 9C). After infusion at moderate rates, normal globin chain ratios of 0.95 to 1.19 were observed at 12 hours. Thus, a reduced dose, while still stimulating fetal globin, is more effective in increasing total hemoglobin and hematocrit than doses typically used for continuous therapy.

Example 14
Short Pulses of Butyrate do not Aggravate Apoptosis.

Peripheral blood from a patient with Hb-E beta thalassemia has 1200 NRBCs per 100 white blood cells which allows for rapid monitoring for apoptosis. This is demonstrated by the red stain which detects fragmented DNA. Apoptosis in cells after high-dose butyrate is demonstrated by red staining of most cells. After low-dose pulse therapy, no red-staining erythroblasts are observed. Short pulses of butyrate do not aggravate the tendency to accelerated apoptosis that is characteristic of thalassemic erythroblasts. A plateau or even a decline in hematologic response has been observed when butyrate therapy is given continuously.

This effect was observed in a patient with $\beta°$ thalassemia who responded to weekly pulse butyrate with an increase in fetal globin synthesis and improved globin chain balance from 0.5 to 0.85 non-$\alpha$/$\alpha$ globin chain ratios. A three fold increase in $\gamma$ globin mRNA was detected 24 to 36 hours after therapy.

A 1.0 to 1.5 gram per deciliter rise in total hemoglobin followed the increase in $\gamma$ globin mRNA synthesis for 30 to 50 days, but total Hgb plateaued and even declined slightly (FIG. 8). A decline in ferritin was also frequently observed (FIG. 10) even though the patient received single daily supplements.

Figure 10:
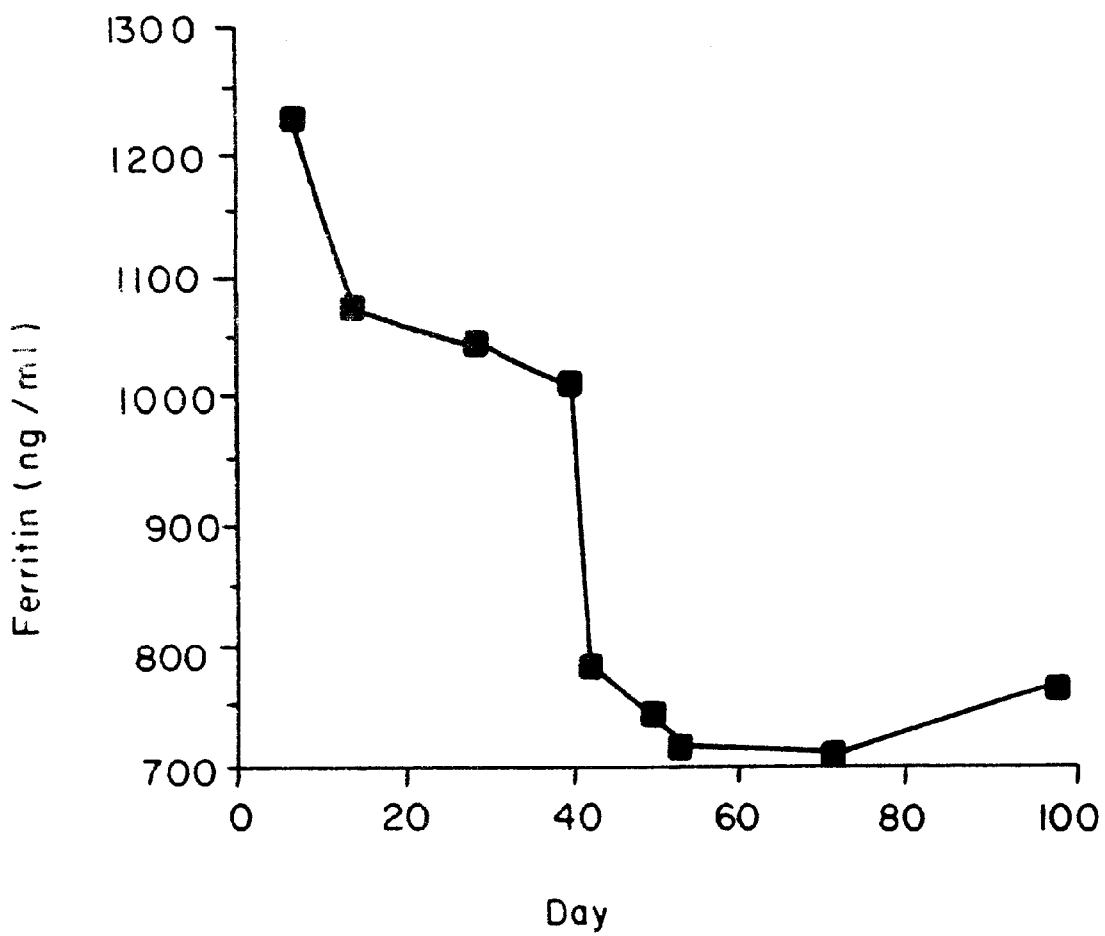
FIG. 10. Ferritin levels of a patient under therapy.

When therapy was decreased to shorter pulses for two to three days on alternate weeks, total hemoglobin rose another two grams per deciliter for 50+ days (FIG. 8). Increased iron supplements were required to support active erythropoiesis, despite the iron overload (FIG. 10).

Other embodiments and uses of the invention will be apparent to those skilled in the art from consideration of the specification and practice of the invention disclosed herein. All U.S. patents, patent application and other documents cited herein, for whatever reason, are to be specifically incorporated by reference. The specification and examples should be considered exemplary only with the true scope and spirit of the invention indicated by the following claims.

I claim:

1. A method for stimulating the expression of a globin protein or the proliferation or development of erythroid cells, myeloid cells, or megakaryotic cells in a subject, comprising administering to the subject in need there of an effective amount to result in said stimulation of a composition comprising (1) as its active ingredient a compound selected from the group consisting of proprionyl hydroxamate, butyryl hydroxamate, suberoyl bis hydroxamic acid and pharmaceutically acceptable salts thereof and (2) a pharmaceutically acceptable carrier or diluent.

2. The method of claim 1 wherein said subject is suffering from anemia.

3. The method of claim 1 wherein the compound is administered in pulsed administrations, wherein said administrations comprise a plurality of pulses, wherein said pulses are the same effective dose at a reduced administration frequency when compared to a discontinuous multiple administration of said compound, or administration of a reduced dosage of said compound when compared to discontinuous multiple administration of said compound.

4. The method of claim 3, wherein an interval between each pulse is greater than 48 hours.

5. The method of claim 3, wherein an interval between each pulse is greater than the in-vivo half-time of said compound.

* * * * *